(12) United States Patent
Ascenzi

(10) Patent No.: US 8,880,385 B2
(45) Date of Patent: Nov. 4, 2014

(54) METHOD AND SYSTEM FOR MODELING BONE STRUCTURE FROM COLLAGEN BUNDLE ORIENTATIONS

(75) Inventor: Maria-Grazia Ascenzi, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 569 days.

(21) Appl. No.: 12/809,509

(22) PCT Filed: Dec. 19, 2008

(86) PCT No.: PCT/US2008/087797
§ 371 (c)(1),
(2), (4) Date: Oct. 7, 2010

(87) PCT Pub. No.: WO2009/086176
PCT Pub. Date: Jul. 9, 2009

(65) Prior Publication Data
US 2011/0022370 A1    Jan. 27, 2011

Related U.S. Application Data

(60) Provisional application No. 61/008,823, filed on Dec. 21, 2007.

(51) Int. Cl.
| | | |
|---|---|---|
| *G06F 9/455* | (2006.01) | |
| *G06F 19/10* | (2011.01) | |
| *G06T 7/20* | (2006.01) | |
| *G06T 7/00* | (2006.01) | |
| *G06F 19/00* | (2011.01) | |

(52) U.S. Cl.
CPC . *G06F 19/10* (2013.01); *G06T 7/20* (2013.01); *G06T 7/0012* (2013.01); *G06F 19/3437* (2013.01)
USPC ............................... 703/11; 702/19; 382/128

(58) Field of Classification Search
CPC ... G06F 19/10; G06F 19/3437; G06T 7/0012; G06T 7/20
USPC ............................................ 703/11; 382/128
See application file for complete search history.

(56) References Cited

U.S. PATENT DOCUMENTS

| | | | |
|---|---|---|---|
| 6,023,659 A * | 2/2000 | Seilhamer et al. | ............... 702/19 |
| 7,124,067 B2 | 10/2006 | Ascenzi | |
| 7,127,383 B2 | 10/2006 | Ascenzi et al. | |
| 7,212,958 B2 | 5/2007 | Ascenzi et al. | |
| 7,283,940 B2 | 10/2007 | Ascenzi et al. | |
| 7,353,153 B2 | 4/2008 | Ascenzi et al. | |
| 2002/0082779 A1 | 6/2002 | Ascenzi et al. | |
| 2002/0155162 A1 | 10/2002 | Ascenzi et al. | |
| 2003/0216899 A1 | 11/2003 | Ascenzi et al. | |
| 2004/0062786 A1 | 4/2004 | Ascenzi et al. | |
| 2005/0131662 A1 | 6/2005 | Ascenzi et al. | |
| 2008/0208550 A1 | 8/2008 | Ascenzi | |

OTHER PUBLICATIONS

International Search Report mailed on Jun. 30, 2009, for International Application No. PCT/US2008/087797 filed on Dec. 19, 2008, 3 pages.
Ascenzi et al., "Collagen orientation patterns in human secondary osteons, quantified in the radial direction by confocal microscopy," Journal of Structural Biology, 2006, vol. 153, pp. 14-30.
Ascenzi et al., "Mathematical modeling of secondary osteons," Scanning, vol. 26, pp. 25-35, 2004.
Ascenzi et al., "Orientation of collagen at the osteocyte lacunae in human secondary osteons," J. Biomech., 2008, vol. 41(16), pp. 3426-3435.
Ascenzi et al., "Structural differences between "dark" and "bright" isolated human osteonic lamellae" J. Struct. Biol, 141: 22-33, (2003) doi: 10.1016/S1047-8477(02)00578-6.
Bonivtch et al., "Tissue strain amplification at the osteocyte lacuna: a microstructural finite element analysis," J. Biomech., 2007, vol. 40, pp. 2199-2206.
Jasiuk et al., "Modeling of bone at single lamella level," Biomechanics and Modeling in Mechanobiology 3, 2004, pp. 67-74.
Prendergast et al., "Microdamage and osteocyte-lacuna strain in bone: A microstructural finite element analysis," J. Biomech. Eng., Trans. ASME, 1996, 118, 240-246.

\* cited by examiner

*Primary Examiner* — Michael Borin
(74) *Attorney, Agent, or Firm* — Kilpatrick Townsend & Stockton LLP

(57) ABSTRACT

The present invention relates to the characterization of human bone microstructure that is applicable to methods of characterizing and predicting fracture initiation, propagation, and arrest. These methods involve the collagen orientation in proximity of osteocyte lacunae, such as the lacunar-ECM interface and perilacunar region, and the role that collagen orientation plays in micro-biomechanics. In particular, collagen orientation at the lacuna-matrix interface optimizes the magnitude of stresses during the elastic phase. Further, the role of collagen-apatite orientation at the interface between matrix and osteocyte lacuna delays micro-crack initiation, propagation, and arrest.

12 Claims, 12 Drawing Sheets

Fig. 1
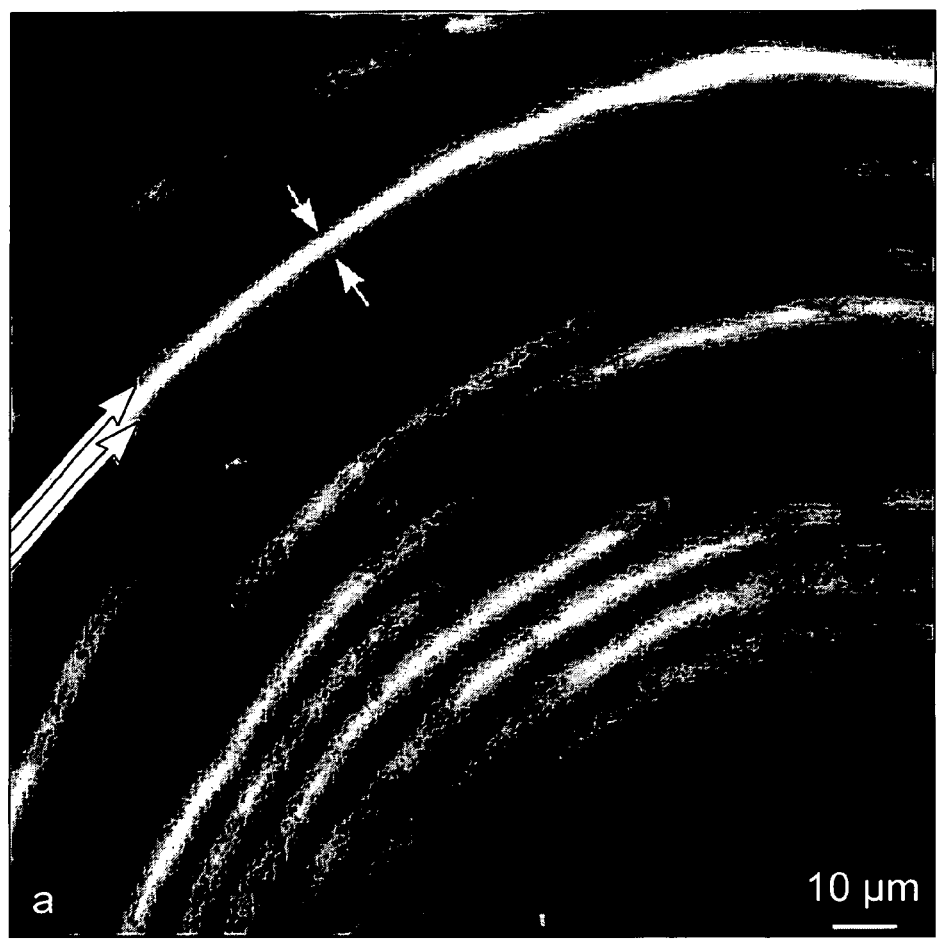
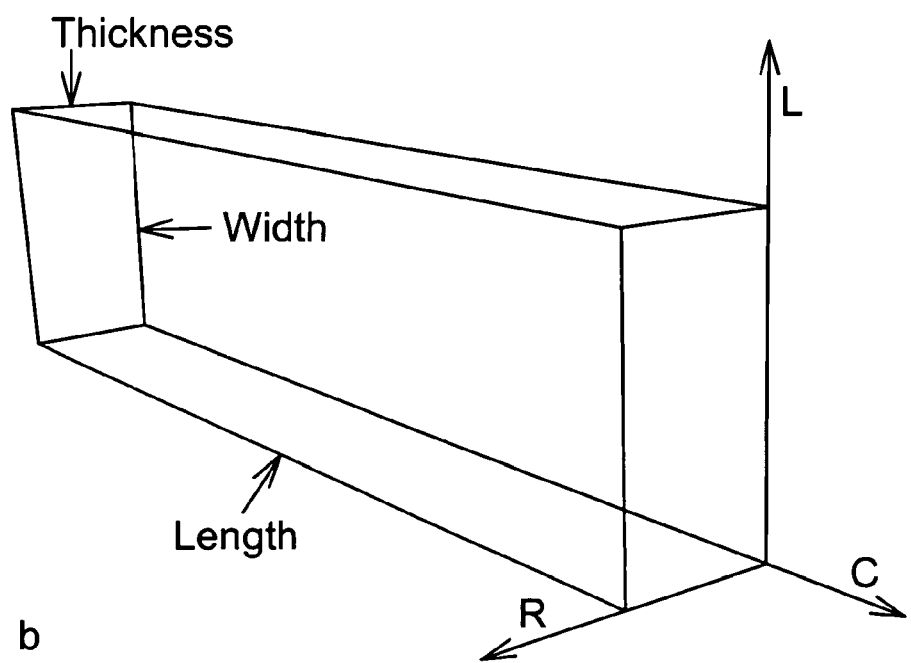

Fig. 3
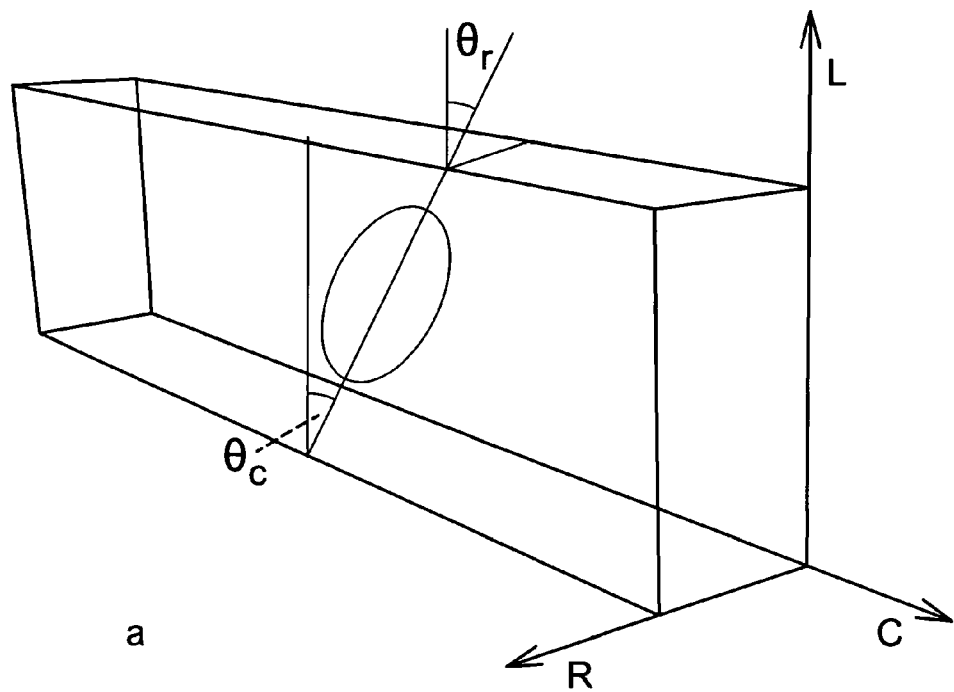
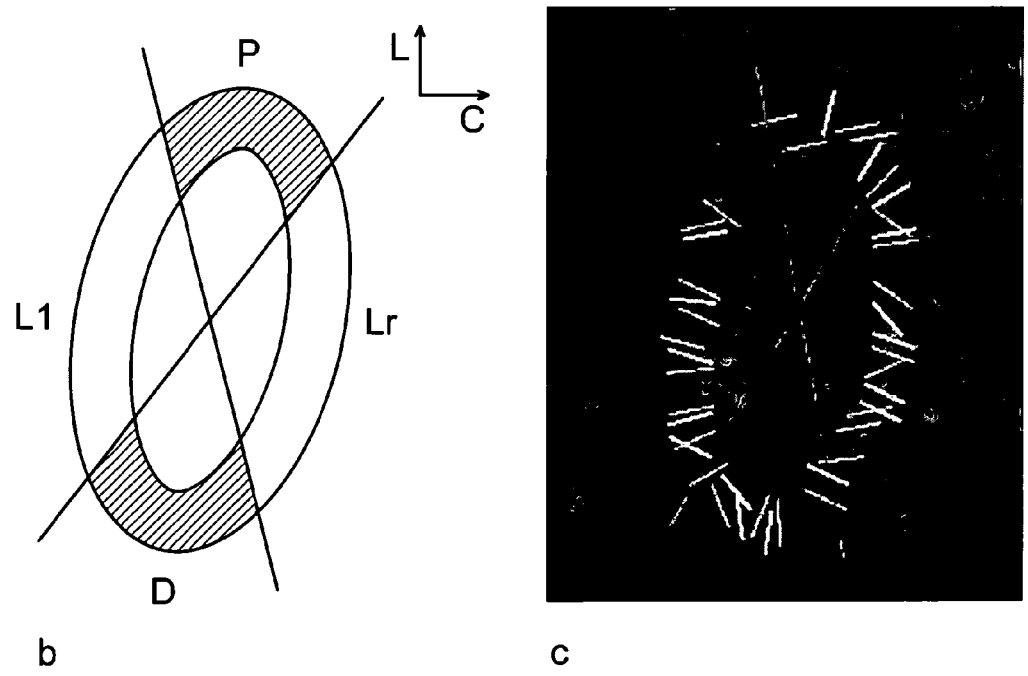
a
b
c

Fig. 4
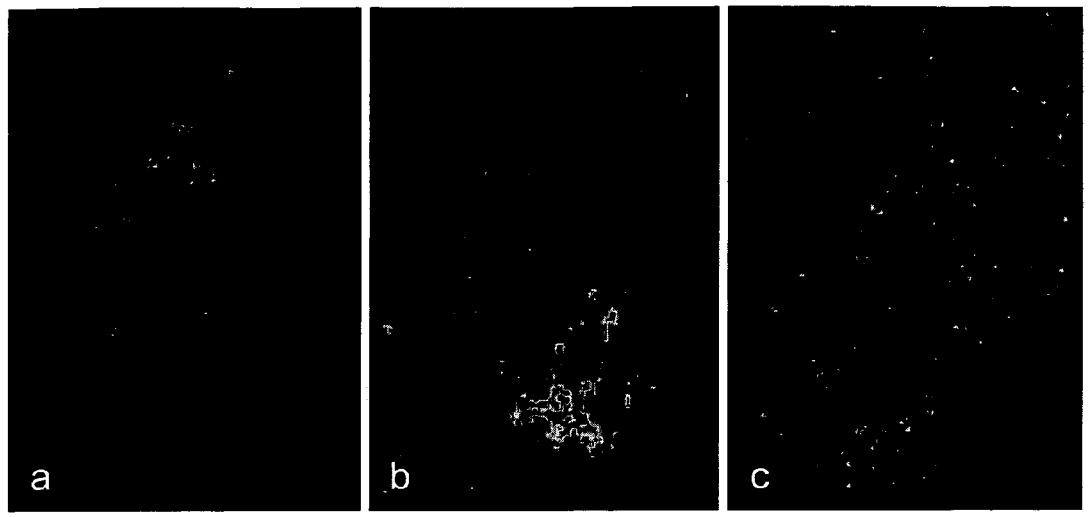
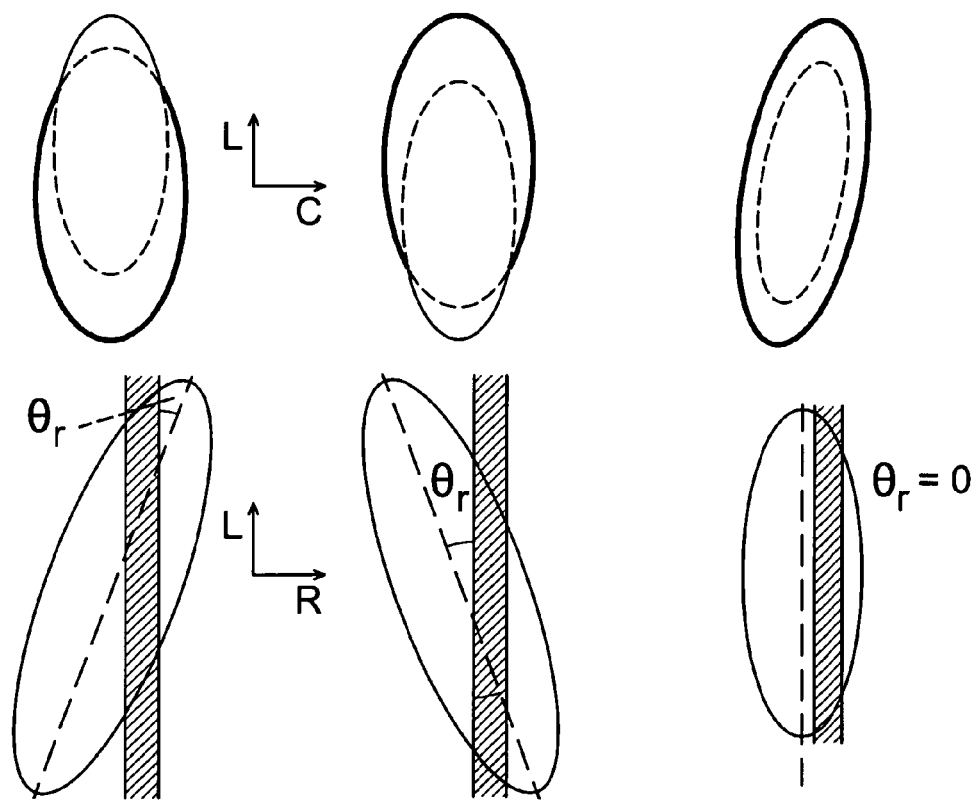

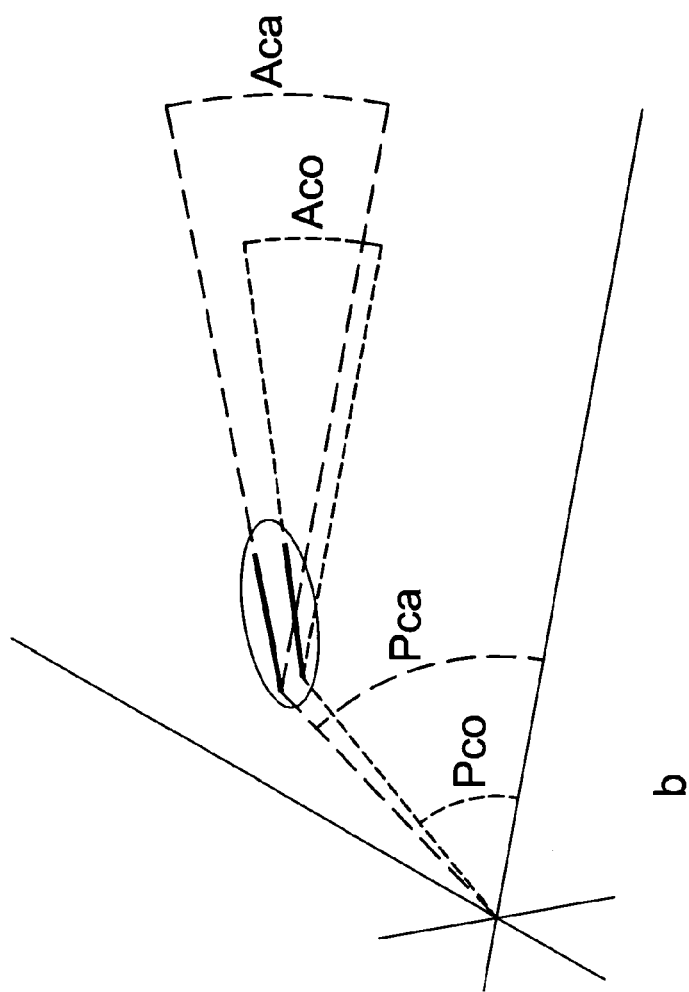
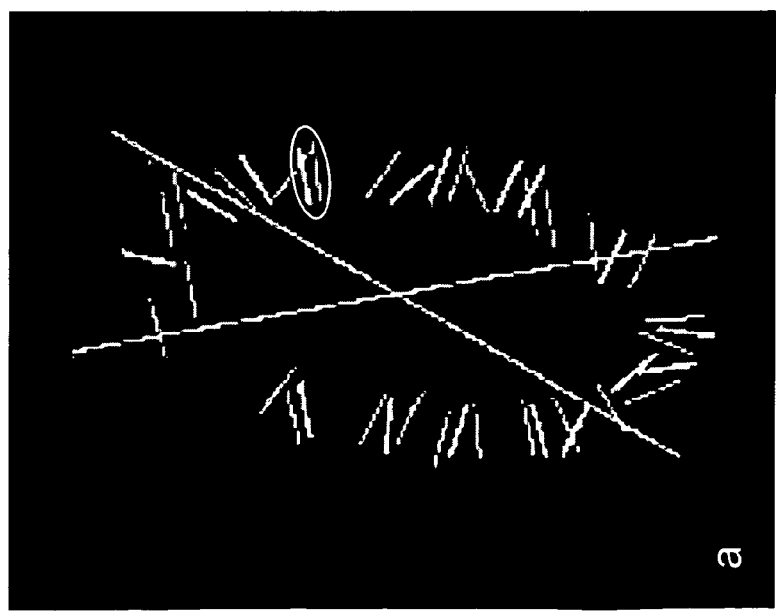
Fig. 7 (Sheet 1)

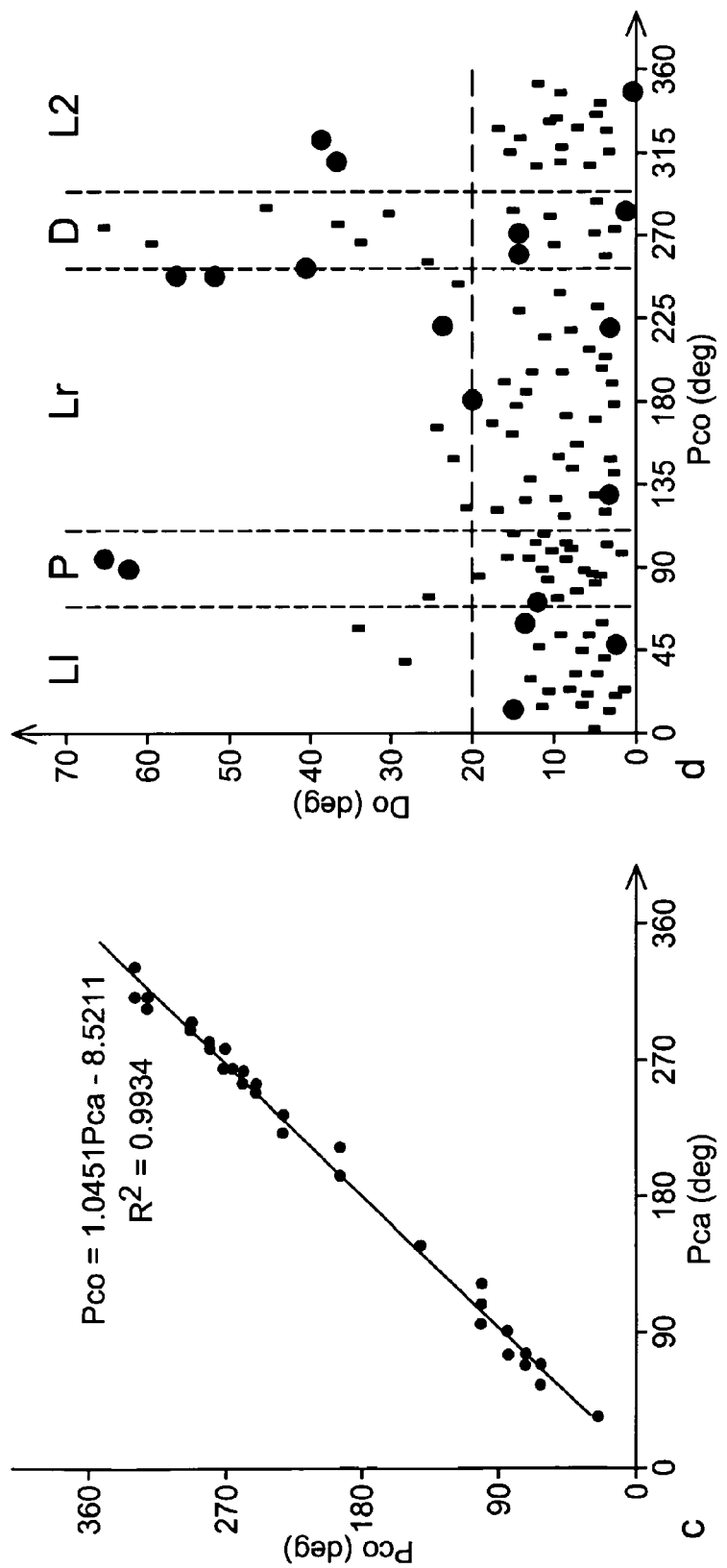
Fig. 7 (sheet 2)

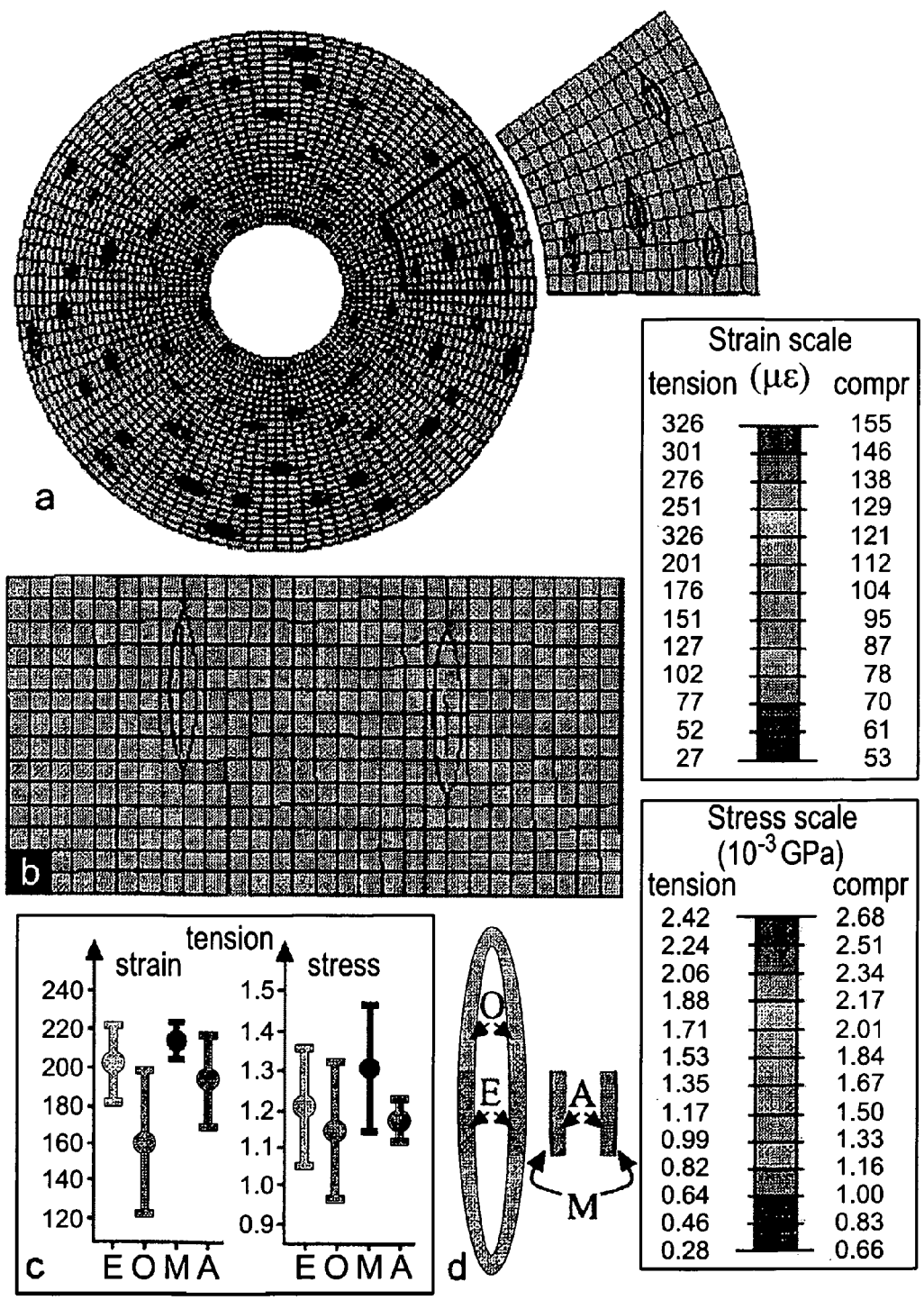
Fig. 8 (Sheet 1)

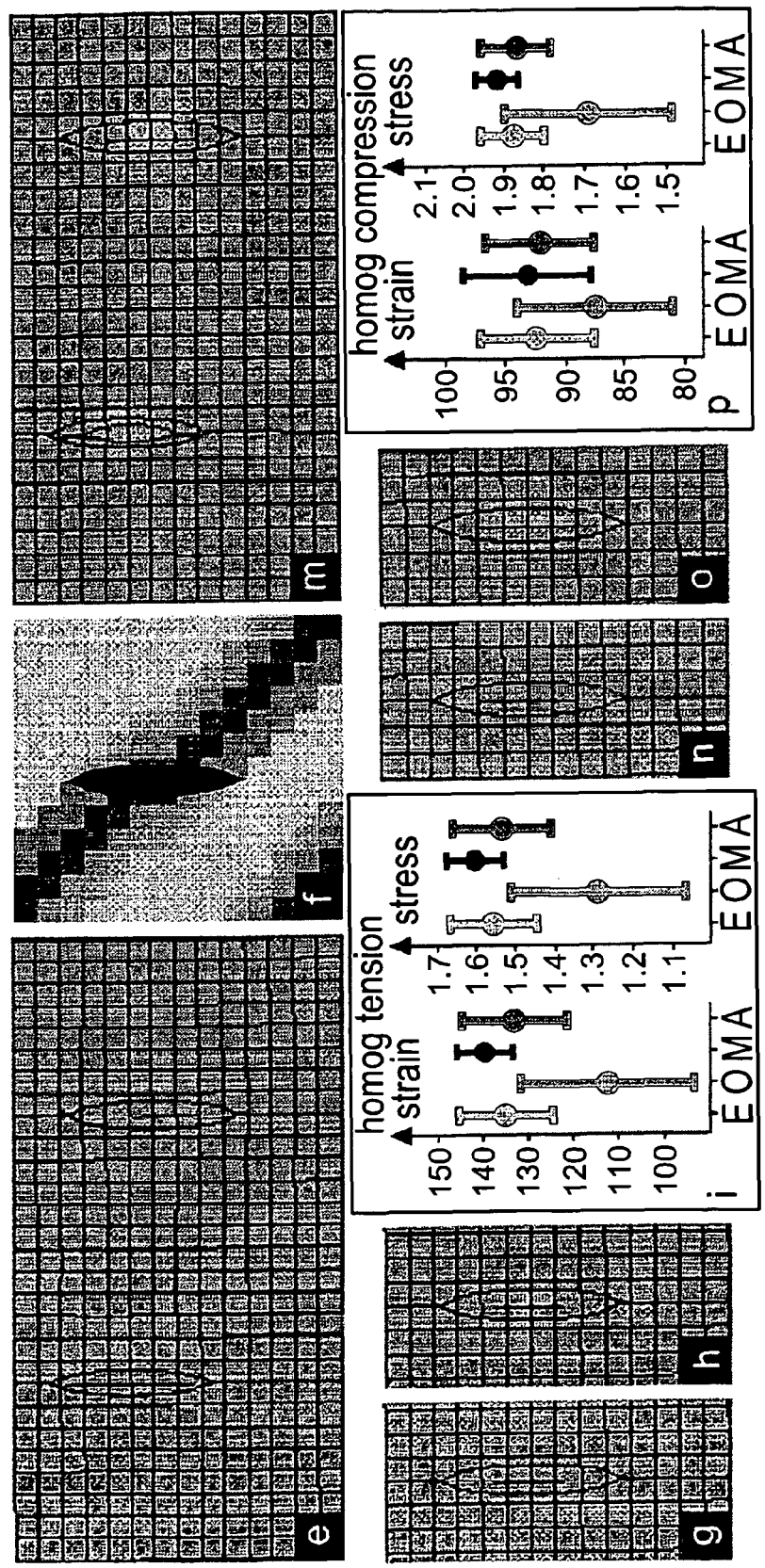
Fig. 8 (Sheet 2)

Fig. 8 (Sheet 3)
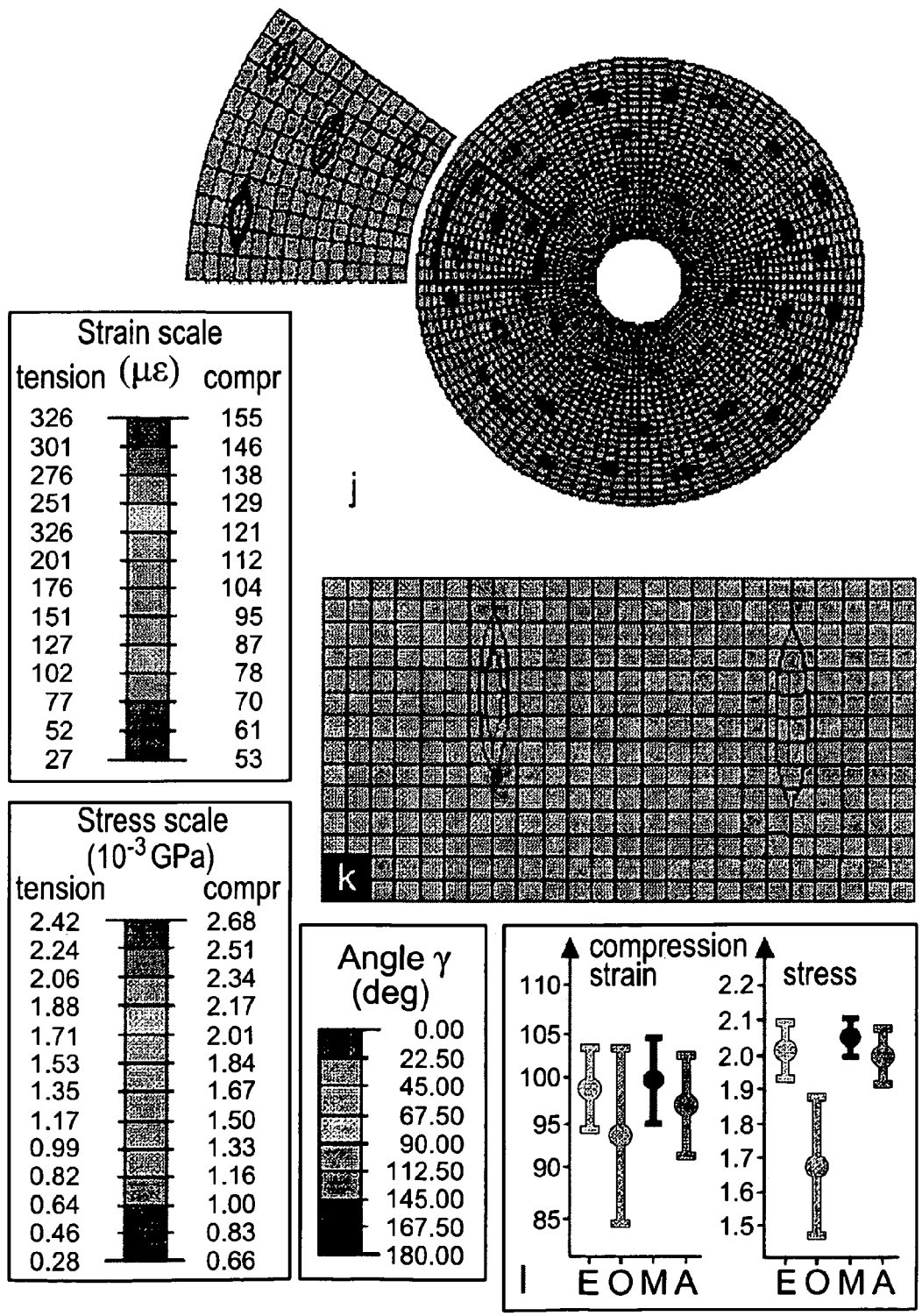

METHOD AND SYSTEM FOR MODELING BONE STRUCTURE FROM COLLAGEN BUNDLE ORIENTATIONS

This application claims the benefit of priority to U.S. Provisional Patent Application No. 61/008,823, filed Dec. 21, 2007, which is hereby incorporated by reference in its entirety.

This invention was made with Government support of Grant No. CMS-0075055 awarded by the National Science Foundation. The Government has certain rights in this invention.

FIELD OF THE INVENTION

The present invention relates to characterizations of human bone micro-structure that are pertinent to understanding fracture initiation, propagation, and arrest. More specifically, the present invention comprises a method and system for modeling the hierarchical structure of bone based on collagen bundle orientations, wherein the model can be used, e.g., to characterize and predict fracture initiation, propagation, and arrest in a bone. Further, the present invention shows that the orientation of elementary components in proximity of osteocyte lacunae is definite and plays a role in influencing secondary osteon micro-biomechanics.

BACKGROUND

Leeuwenhoek (1693) was the first author to report on the osteocyte lacuna. The first observation of osteocyte lacuna raised the significance of geometry to bone microstructure by noting the necessity of proper direction of specimen cut to observe the pseudo-ellipsoidal shape of the lacuna (Leeuwenhoek, 1693). In the osteocyte lacuna, the osteocyte processes extend through the surrounding extracellular matrix (ECM) within so-called canaliculi (Enlow, 1962). Modern observations show canalicular distribution at the perilacunar region (Martin et al., 1998). Several hypotheses have been so far formulated relative to a correlation between densities of osteocyte lacunae and distributions of properties of bone tissue related to strain, remodeling or metabolism (Skedros et al., 2005). The osteocyte lacunae have been hypothesized to act as stress concentrators through their ellipsoidal contour and as fracture initiators when a crack forms at the apex by deformation (Currey, 1962; Piekarski, 1970). Reilly (2000) and O'Brien et al. (2005a and 2005b) observed micro-damage around the osteocyte lacunae with micro-cracks accumulating at a rate that increased with the strain/stress level. Prendergast and Huiskes (1996) and Bonivtch et al. (2007) investigated the perilacunar strain levels with homogeneous material modeling of the ECM.

Because carbonated apatite crystals in osteons locally follow the orientation of the adjacent collagen (Ascenzi A. et al., 1966), and because the collagen-apatite orientation is one of the variables that determines the mode of fracture (Simkin and Robin, 1974), collagen orientation is an important datum to understand fracture initiation, propagation, and arrest in osteons and in particular in connection with osteocyte lacunae. The osteon model of the present invention includes the collagen orientation datum at the lacunar-ECM interface, a new step in the long history of osteon modeling (from Gebhardt, 1906 to Jasiuk and Ostoja-Starzewski, 2004; Ascenzi and Lomovstev, 2006). Each of extinction or brightness of lamellae outside the perilacunar region denotes a specific dominant orientation of collagen in cross-section under circularly polarized light (Ascenzi and Lomovstev, 2006). Indeed, the dominant collagen orientation of so-called extinct lamellae forms small angles with the original osteon axis, while the dominant collagen orientation in bright lamellae forms larger angles. The osteon model presented here incorporates the collagen orientation in the lamella within and beyond the perilacunar region.

The present invention is based on the following: (i) the collagen orientation patterns along the lateral regions of the osteocyte lacuna do not differ in relation to type (extinct or bright) of lamellae on the osteonal cross-section under circularly polarized light; (ii) the generally circumambiently perpendicular orientation of collagen at the perilacunar equatorial section of the lacuna of both lamellar types reinforces bone tissue to better resist stress generated under tensional loading; and (iii) the tilt of the lacuna, radial and circumferential, depends on the lamellar type—e.g., the osteocyte lacuna is more likely to be tilted with respect to the lacunar walls in extinct lamella than in the bright lamella. At the apices of such lacuna, collagen is more likely to follow the adjacent canalicular orientation in the bright lamella, in order for the parallel apatite to reinforce the tissue. This would delay fracture initiation and therefore optimize tissue function.

SUMMARY OF THE INVENTION

The present invention comprises a method of predicting a mechanical response of a subject bone osteon to an applied force comprising the steps of: (a) identifying a subject bone osteon; (b) selecting at least one database comprising empirical data corresponding to recorded observations of canal diameter, osteon diameter, positions and dimensions of lacunae, collagen bundle orientations in a selected region of the subject bone osteon; (c) using the database with a computer program to generate a simulated region of the subject bone osteon, the simulated region comprising at least one simulated microstructural element, wherein the computer program performs the steps of: (1) defining a simulated three-dimensional region corresponding to the simulated microstructural element of the simulated region of the subject bone osteon; (2) creating a finite element mesh defining a finite number of three-dimensional elements filling the simulated three-dimensional region; and (3) assigning at least one property to each of a plurality of the elements in the finite element mesh using data from the database; (d) using a computer program to predict a mechanical response of the region of the subject bone osteon to an applied force, wherein the computer program performs the steps of: (1) generating a simulated force applied to the simulated three-dimensional region; (2) calculating a response to the simulated force for each of the plurality of elements in the finite element mesh using the at least one assigned property for each element; (3) computing a response of the simulated three-dimensional region to the simulated force using the calculated responses of the plurality of elements in the finite element mesh; (4) computing the mechanical response of the simulated region of the subject bone osteon from the computed response of the simulated three-dimensional region to the simulated force; and (5) outputting the computed mechanical response of the region of the subject bone osteon to the simulated force.

The present invention also comprises a computerized bone model stored on one or more computer readable media for predicting a mechanical response of a region of a subject bone osteon to an applied force, comprising: (a) a database comprising empirical data corresponding to recorded observations of canal diameter, osteon diameter, positions and dimensions of lacunae, collagen bundle orientations in a selected region of the subject bone osteon; and (b) a set of computer readable instructions for use with the database comprising: (1) instructions for generating a simulated region of the subject bone osteon wherein the simulated region comprises at least one simulated microstructural element; (2) instructions for defining a simulated three-dimensional region corresponding to the simulated microstructural element of the simulated region of the subject bone osteon; (3) instructions for creating a finite element mesh defining a finite number of three-dimensional elements filling the simulated three-dimensional region; (4) instructions for assigning at least one material property to each of a plurality of the elements in the finite element mesh using data from the database; (5) instructions for applying a simulated force to the simulated three-dimensional region; (6) instructions for calculating a response to the simulated force for each of the plurality of elements in the finite element mesh using the assigned at least one property for each element; (7) instructions for computing a response of the simulated three-dimensional region to the simulated force using the calculated responses of the plurality of elements in the finite element mesh; (8) instructions for computing the mechanical response of the simulated region of the subject bone osteon from the computed response of the simulated three-dimensional region to the simulated force; and (9) instructions for outputting the computed mechanical response of the region of the subject bone osteon to the simulated force.

In one embodiment of the methods or models of the present invention, the selected region of the subject bone osteon is the interface between osteocyte lacunae and calcified extracellular matrix (ECM) in a secondary osteon. In another embodiment, the collagen bundle orientation is circumambiently perpendicular along the lateral side of the lacunar-ECM interface. In another embodiment, the collagen bundle orientation at the perilacunar region is circumambiently perpendicular to the lacuna. In another embodiment, the selected region of the subject bone osteon comprises a sharp or round apex of lacuna. In another embodiment, the empirical data comprises a stress distribution generated by the collagen bundle orientation.

Further, new data at the perilacunar region concerning orientation of collagen-apatite, and prior data on collagen orientation outside the perilacunar region, are incorporated in a novel simulation of osteons to investigate how orientation relates to strains and stresses during mechanical testing. The perilacunar region was observed by confocal microscopy within single lamellar specimens, isolated from osteons. The specimens were separated by extinct or bright appearance in transverse section under circularly polarizing light. This is because synchrotoron diffraction and confocal microscopy had established that each type, away from the perilacunar region, corresponds to specific dominant collagen orientation (extinct lamellae's dominant collagen forming small angles with the original osteon axis, while the bright lamellae's forms larger angles). Morphometry of serial confocal images of each perilacunar region showed collagen orientation generally following the orientation of canaliculi, circumambiently-perpendicular to the lacuna. The lacunae tilted relative to the lamellar walls were more numerous in extinct than in bright lamellae. Their apices were less likely in extinct than bright lamella to show collagen following the canlicular orientation. The simulation of osteocyte lacunae in osteons, under tension or compression loading, supports the idea behind the present invention that collagen orientation affects strains and stresses at the equatorial perilacunar region in conjunction with the presence of the lacuna. Further, it further appears that collagen orientation diverts propagation of micro-cracks initiating from apices.

BRIEF DESCRIPTION OF THE DRAWINGS

FIG. 1. (a) This cross-sectional detail of secondary osteon is viewed transversely to the osteon axis. The lamellae appear alternatively bright and extinct under circularly polarized light observed at 260×. The arrows indicate the orientation of the circumferential excisions, and the white arrowheads indicate the thickness of a lamella. (b) This diagram not to scale shows the orientation of an isolated lamellar specimen in relation to its original orientation within the osteon prior to lamellar isolation: radial (R), circumferential (C) and longitudinal (L) directions. The osteon in (a) is viewed on the RC-plane in (b). Lamellar length (230±40 µm), thickness (70±3 µm) and width are indicated. Lamellar width varies between 4 and 16 µm, with extinct lamellae generally thicker than bright lamellae.

FIG. 3. (a) The angles $\theta_r$ and $\theta_c$ are defined to specify the orientation of the lacuna with respect to the isolated lamellar specimen and to the original osteon prior to specimen isolation: longitudinal (L), circumferential (C) and radial (R) directions. $\theta_r$ is the angle projection between the major axis of the osteocyte lacuna and the L axis on the LR plane, and $\theta_c$ is the angle projection between the major axis of the osteocyte lacuna and the L axis on the LC plane. (b) To conduct morphometry, an ellipse tilted by $\theta_c$ is fitted to the lacuna-matrix interface (light inner border), and a larger ellipse (darker outer border) is drawn 3 µm away from the first ellipse. The two lines at 70° and 100°, respectively, in reference to the ellipse's minor axis divide the perilacunar region in proximal (P), distal (D), lateral left (Ll) and lateral right (Lr) regions. (c) Segments within the chosen 3 µm zone show orientation of collagen (thinner segments) and canaliculi (thicker segments) on confocal image (1707×) of bright specimen #3.

FIG. 4. The apices of lacunae (a) and (b) appear at a slight difference in focus. In (a), top apex appears more elongated and bottom apex more stout. The opposite occurs in (b) and no difference between the focus on the two apices is observed in (c). The first row of corresponding diagrams (not to scale) further illustrates for each of (a) through (c), the lacunar shape on the same circumferential-axial reference plane. Each continuous ellipse represents the optical section at the beginning, and each segmented ellipse represents the optical section at the end, of the plane of focus of thickness 0.5 µm. The diagrams at the bottom row explain the appearance in terms of optical section on the radial-longitudinal plane at the two end-planes of the section, shaded grey.

FIG. 7. (a) For the two segments (in dark grey), one representing a canaliculus (thicker) and one representing collagen (thinner) for the image at FIG. 3c from the stack relative to bright specimen #3, (b) the polar angle is indicated (Pca for the canaliculus and Pco for collagen) with respect to center and minor axis of the ellipse superimposed on the lacunar image. (c) The angle Pca (in degrees) of each canaliculus at its first appearance at the lacunar-matrix interface, is mapped with respect to the angle Pco (in degrees) of the adjacent collagen for bright specimen #3. An $R^2$=0.9934 and the best-to-fit the line of equation Pco=1.0451*Pca−8.5211 show that both canaliculi and collagen bundles are locally circumambiently-perpendicular to the lacunar wall. (b) The absolute value of the difference, measured in degrees, in orientation between canaliculus and adjacent collagen (Do), with Do=|Aca−Aco| where Aca and Aco are described in (b), is here mapped with respect to the angle Pco of collagen for the eight images for specimen #3. Among all the points that come from the stack of images of this lacuna, the larger dots indicate the points obtained from (a).

FIG. 8. This series of images shows strain and stress distributions on a modeled osteon containing lacunae under either tension (a through i) or compression (j through p) along the osteon axis under the same load (10 gr) within the elastic range. Meshing represents finite elements. (a) Under tension, maximum principal strains are shown on a complete transverse section with an enlarged detail and (b) a hemi-longitudinal section containing two lacunar sections. (c) This diagram show the mean (dot) and standard deviation (bar) of strain and Mises stress fields in the perilacunar region (d): (E) equatorial, (O) outside equatorial, (M) mid-equatorial, and (A), away from M in E. The distribution of Mises stresses relative to (b) is shown in (e). (f) This diagram shows the local collagen orientation on a detail of undeformed longitudinal section relative to (b) and (c). (g) Lower strains and (h) higher stresses are present in the homogeneous model than in the composite model (compare (i) with (c)). (j) Under compression, maximum principal strains are shown on a complete transverse section with an enlarged detail and (k) a detail of a longitudinal hemi-section containing two lacunae. (l) Mean (dot) and standard deviation (bar) for strain and stress fields under compression in perilacunar region (d). The distribution of Mises stresses relative to (k) is shown in (m). (n) Lower strains and (o) lower stresses are present in the homogeneous model than in the composite model (compare (p) with (l)).

DETAILED DESCRIPTION OF THE INVENTION

Figure 2:
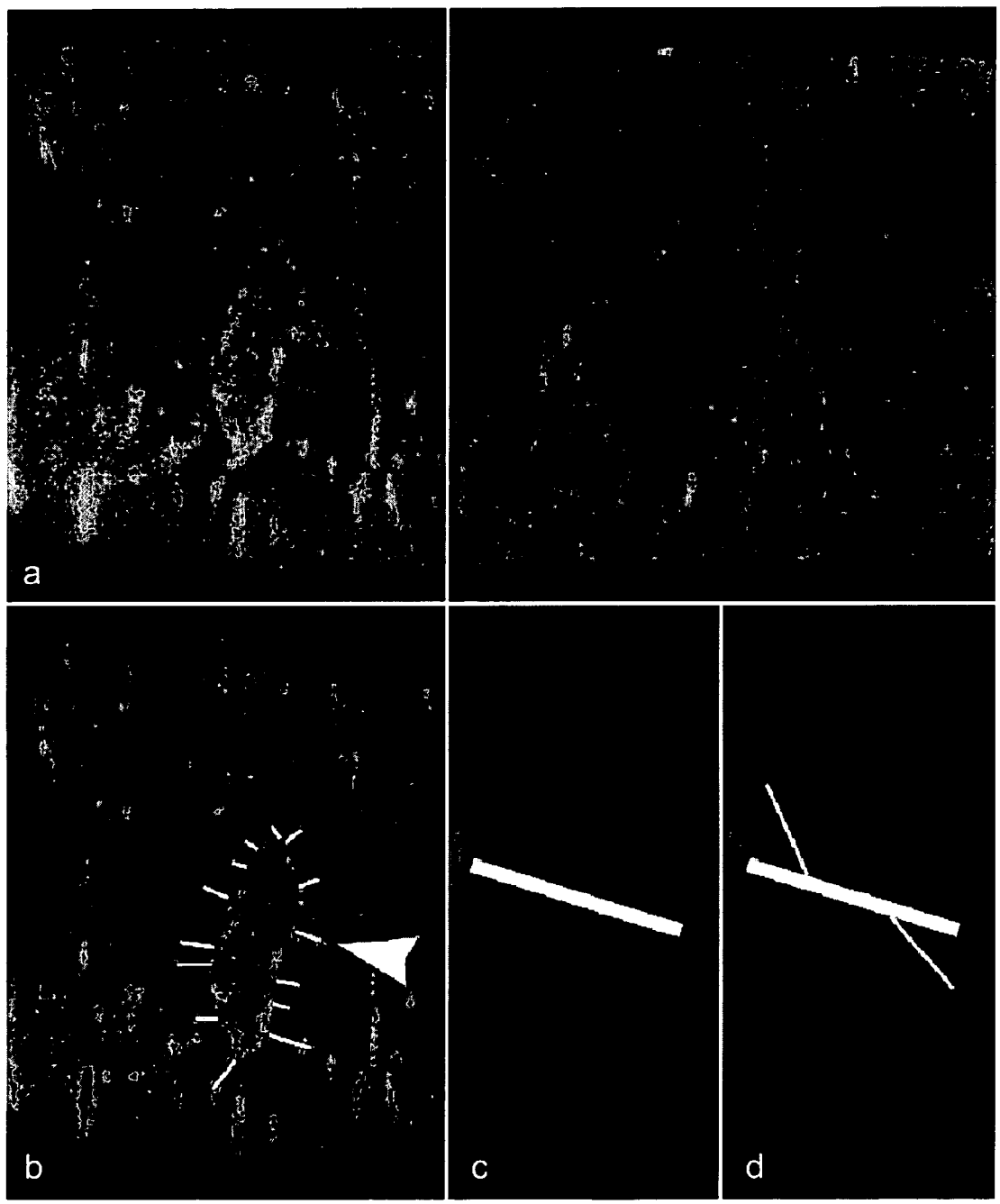
FIG. 2. (a) This confocal image shows an osteocyte lacuna (in rectangle) on an extinct lamellar specimen (629×) by confocal microscopy. Canaliculi are visible through endogenous fluorescence exiting the lacuna and throughout the lamellar specimen. (b) A white segment was super imposed on each canaliculus in focus exiting the lacuna within the rectangle in (a). The arrowhead in (b) points to a segment overlapping a canaliculus enlarged (7.8×) in (c). (d) A thinner white segment was overlapped on each of the two collagen bundles in focus (visible in (c)), that are adjacent to the marked canaliculus.

The present invention relates to an aspect of bone microanatomy with applicability to studies of fracture initiation, propagation, and arrest. Specifically, it involves collagen orientation in secondary osteons at the interface between osteocyte lacunae and calcified extracellular matrix (ECM) by laser scanning confocal microscopy on lamellar specimens isolated by micro-dissection. Further, it explores the role of collagen orientation in the stress distribution at the lacunar-ECM interface by simulation of mechanical testing through finite element analysis (FEA) of an osteon model containing osteocyte lacunae (i.e. by finite element simulation of mechanical loading of single osteons).

Confocal microscopy of single lamellar specimens isolated from human secondary osteons visualized collagen bundles at the perilacunar region. Morphometry performed on images of serial parallel planes of focus through each lacuna showed collagen orientation patterns that followed the orientation patterns of osteocyte canaliculi exiting the lacuna. Both were observed to be circumambiently perpendicular to the lacuna, i.e., locally perpendicular to the lacuna-matrix interface. The collagen distribution patterns associated with each of the two lamellar types did not differ. However, orientation patterns differed between the two lamellar types at the apices of the lacunae tilted with respect to the lamellar walls. First, the lacunae tilted with respect to the lamellar walls are more numerous in extinct lamellae than in bright lamella. Second, the apices of such lacunae are less likely in the extinct lamella than in the bright lamella to show collagen following the canalicular orientation. The micro-structural observations support a first simulation of the behavior of single, fully-calcified osteons under either tension or compression loading that includes the experimentally observed collagen orientation distribution in lamellae away from the lacunae and at the lacuna-matrix interface. The simulation indicates that the experimentally observed collagen orientation at the lacuna-matrix interface optimizes the magnitude of stresses during the elastic phase. The role of collagen-apatite orientation at the interface between matrix and osteocyte lacuna may delay micro-crack initiation, propagation, and arrest.

EXAMPLES

The present invention is next described by means of the following examples. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Materials and Methods:

The preparation and the imaging of specimens described herein followed the protocol described previously by Ascenzi M.-G. et al., 2003; Ascenzi M.-G. and Lomovtsev, 2006. See also U.S. Patent Application Publication No. 2005/0131662. Briefly, fully calcified lamellae that appeared either bright or extinct in transverse section under circularly polarized light (Amprino and Engström, 1952) were isolated from the mid-femoral shaft of nine young adult male donors (i.e., cadavers) (FIG. 1a). FIG. 1a illustrates the location and direction of cutting along the outer and inner circumferential edges of a lamella (Ascenzi et al., 2003). The cutting edge of the microblade's chiseled ground surface, with a tapered triangular transverse profile, provides a smooth cut on a wet 70 µm-thick section. Because of holding constraints, about half of the lamellar circumferential length is isolated. During isolation, a bright lamellar specimen located between two extinct lamellae continues to appear bright, and the adjacent lamellae continue to appear extinct. Similarly, an extinct specimen and its two adjacent bright lamellae continue to appear respectively extinct and bright during isolation. Accordingly, the specimen is considered free of adjacent lamellae and polishing is not required. Each isolated lamellar specimen was observed flat by confocal microscopy along the original radial direction of the osteon in which the lamellar specimen was embedded (FIG. 1b).

Osteocyte lacunae were identified on 133 confocal images from 16 extinct and 16 bright lamellar specimens by their pseudo-ellipsoidal shape (FIGS. 2a and 2b) and 6 to 25 µm maximum dimension (Piekarski, 1970; Marotti, 1979; Ascenzi M.-G. et al., 2004). Intensely bright canaliculi of a thickness ranging between 0.1 and 1 µm (Atkinson and Hallsworth, 1982) were observed exiting the lacuna. Endogenous fluorescence also renders collagen bundles visible on the confocal images (Ascenzi A. et al., 1966; Ascenzi M.-G. et al., 2006). Complete stacks of lamellar images were collected automatically. As magnification increased, the canalicular network became blurred, while thinner fluorescent elements came into clear view (FIG. 2c). The thinner fluorescent elements were identified as collagen bundles on a background of mucopolysaccharides and glycoproteins by small angle micro-focus synchrotron X-ray diffraction and confocal microscopy on decalcified specimens (Ascenzi et al., 1966; Ascenzi et al., 2003). Confocal observation at both lower and higher magnifications allowed positioning of collagen bundles discerned at higher magnification relative to canaliculi at lesser magnification.

The stacks of confocal images were imported into graphic illustrator XaraX1 software (Xara Group Ltd, UK) calibrated to measure in real microns. For each lacunar image, an ellipse tilted by angle $\theta_c$ (FIG. 3a) was fitted to the lacuna, and a 3 µm thick perilacunar portion of the ECM was delimited by a second coaxial ellipse (FIG. 3b). This region of interest was divided into proximal (P), distal (D), and lateral (Ll on the left, and Lr on the right) to assess the percentage of collagen that parallels locally the canaliculi using two lines forming a 70° and 110° angle with the ellipses' minor axis. Each canaliculus in focus exiting a lacuna was marked as a segment of same orientation and each collagen bundle in focus adjacent to a canaliculus was similarly marked with a thinner segment (FIG. 3c). More specifically, a segment was superimposed to each canaliculus in focus at lower magnification and a thinner segment was superimposed to each adjacent collagen bundle, in focus at higher magnification (FIG. 3c).

After identification of a canaliculus at the perilacunar region, the collagen orientation was analyzed at the site on the plane of focus and considered as following the orientation of the canaliculus if the angle difference was smaller than 20°. Such limit was chosen for consistency with the approximate 20° deviation of canaliculi from distribution precisely perpendicular to the lacunar wall. The intra-observer error was assessed as 0.01, on two observers and one repetition, and the inter-observer error was assessed as 0.02, on five images. The angle $\theta_r$, which represents the tilt of the lacuna with respect to the axis L on the CL plane (FIG. 3a), was assessed as either zero or non-zero by analyzing the perilacunar shapes. A non-zero value of $\theta_r$, on the order of a few degrees, corresponded to a combination of a slight difference in focus between apices and a slender appearance of an apex in comparison to the more stout other apex (FIG. 4). A null $\theta_r$ corresponded to no difference in apices' appearance. A non-zero $\theta_r$ was assessed as $\sin^{-1} (0.5 \text{ n/d})$ where 0.5 µm is the thickness of the plane of focus, n is the number of lacunar images, and d is the distance between the first appearance of the proximal apex and the last appearance of the distal apex on the confocal stack. Further, a combination of a sharper appearance of an apex in comparison to a rounder appearance of the other apex, with a slight difference in focus, was interpreted as a non-zero angle $\theta_r$ between the lacunar major axis and the plane of focus while two apices of same shape were interpreted as a null value for $\theta_r$ (FIG. 4).

Figure 5:
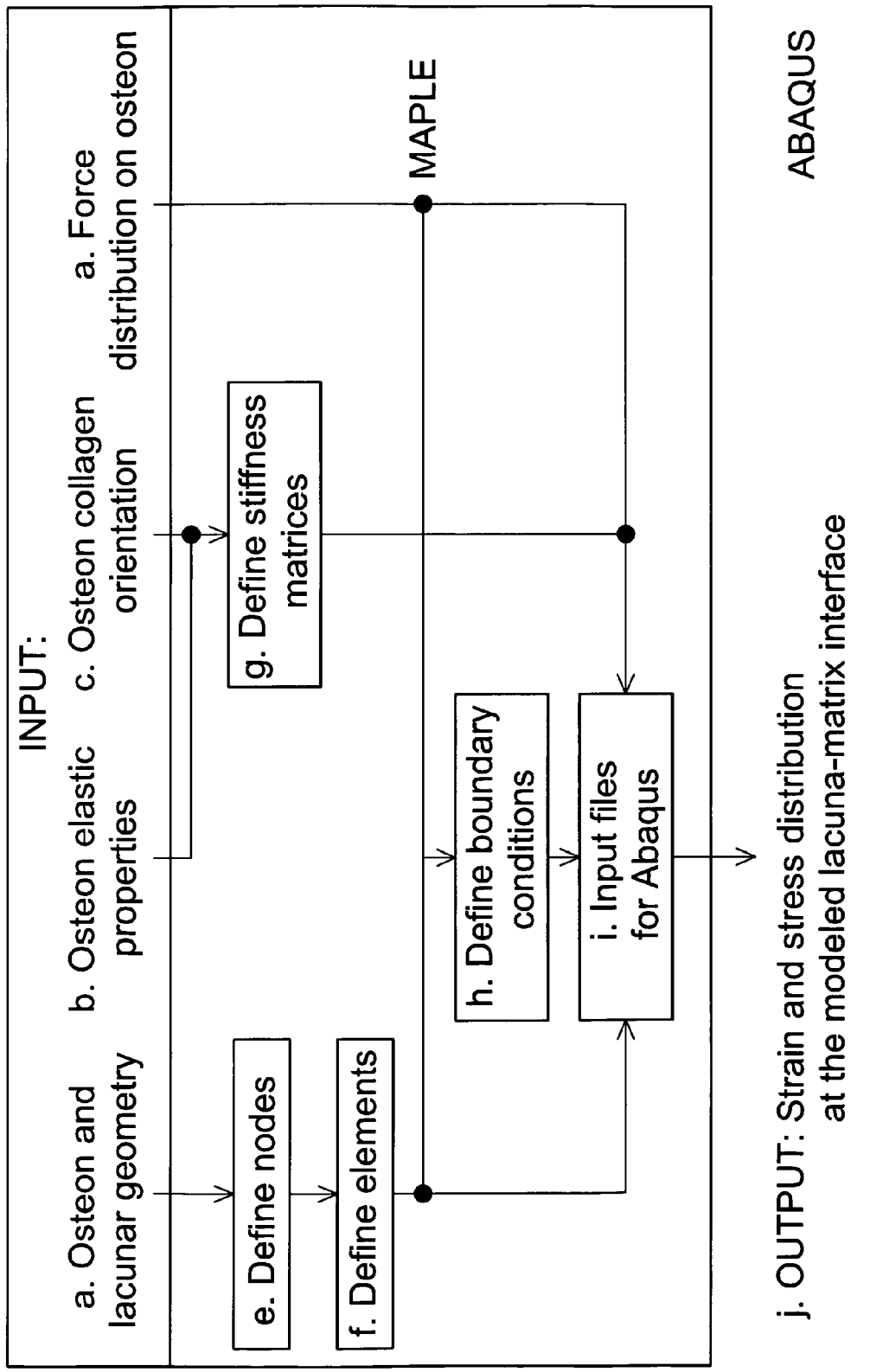
FIG. 5. This chart presents a block diagram of the steps of the model preparation: geometric description, elastic properties relative to loading specifications, collagen orientation distribution are the input for the Maple™ algorithm. Maple™ is programmed to define coordinates of nodes, elements, stiffness matrices, and boundary conditions on files that become the input for Abaqus™ software. Intersection of lines marked with • signifies interaction, as explained in the text. The Abaqus™ output includes the distribution of strains and stresses in the osteon and in particular at the perilacunar region.

The chi-squared test, the inference of proportions for paired comparisons and the t-test, all with significance set at 0.05 for the p-value, assessed statistical differences of lacunar observations between extinct and bright groups. The morphometric data relative to the perilacunar region were included in a series of finite element models that simulated the experimentally observed mechanical behavior of a single secondary osteon (Ascenai and Bonucci, 1967, 1968; Ascenzi et al., 1985, 1997) containing osteocyte lacunae. To probe the role of collagen-apatite orientation, the alternative option was included to assign constant homogeneous material properties to all the elements of the model. When the material properties of an element are chosen to depend on the local collagen orientation defined by the angle γ, the value of γ is entered into the formulae for locally unidirectional composites (Vinson, 1993). The distribution of γ within the model varies according to the osteon type, whether extinct or bright, outside the perilacunar region in accord with Ascenzi and Lomovstev (2006). FIG. 5 summarizes the steps to build the models (FIG. 6), using Maple™ (Waterloo, Inc.) and Abaqus™ (Hibbit, Karlson, and Sorensen, Inc.) software. Maple™ was employed as preprocessor for the FEA carried out by Abaqus™ (FIG. 5).

A thick cylindrical shell, whose specifications followed Ascenzi A. et al. (1997) for tensional loading and Ascenzi A. and Bonucci (1968) for compression, was filled with 20-node elements of mean size 3 µm outside the pseudo-ellipsoids modeling the osteocyte lacunae (FIG. 6) located in the middle portion of the cylindrical shell. The major axis of each pseudo-ellipsoid is aligned to the osteon axis. The total number of elements is on the order of 464,800. The material properties of the ECM were modeled as locally unidirectional fiber composite (Ascenzi M.-G., 1999), where the collagen fibrils represented the composite's matrix, following the material science terminology, and the carbonated apatite crystallites represented the fibers. Because locally the apatite follows the collagen orientation (Ascenzi A. et al., 1966), the apatite orientation is taken to equal the collagen orientation observed in the confocal images. Perfect bonding of elementary components and continuity of tissue was assumed away from the lacunae.

The stiffness matrix (FIG. 5) relative to a specific collagen orientation followed the composite formulation with small displacements (Vinson, 1993; Ascenzi M.-G., 1998). The collagen orientation followed the observed pattern within 3 μm from each lacuna and the previously described distribution (Ascenzi M.-G. and Lomotsev, 2006) away from the lacuna. Because so-called extinct osteon shows in cross-section under circularly polarized light approximately 9% bright area, the collagen orientation of the extinct osteon model is specified by a 9% proportion applied to the percentage distributions of orientations longitudinal, oblique, and transverse for the lamellae that appear respectively bright and extinct. The material properties assigned to the elements were checked to homogenize to an 11.6 GPa elastic modulus along the osteon axis, a 5.5 GPa elastic modulus transverse to the osteon axis, a 4 GPa shear modulus and 0.3 for the Poisson's ratio for tensional loading and to an 6.3 GPa elastic modulus along the osteon axis, a 6.3 GPa elastic modulus transverse to the osteon axis, a 4 GPa shear modulus and 0.3 for the Poisson's ratio for compression loading (Ascenzi A. and Bonucci, 1967, 1968 and 1972; Ascenzi A. et al., 1997) for the whole osteon.

One base of the model was constrained to a plane while loading was applied as a uniform distribution on the other base. Two steps simulated the quasi-static application of two weights to the extensometer used under either tension or compression mode. The model was validated by means of the observed deformation of the osteon (Ascenzi A. and Bonucci, 1968; Ascenzi A. et al., 1985 and 1997).

Preparation of Osteon Model:

To study the strain and stress distribution in relation to the experimentally observed collagen orientation at the perilacunar region, a novel three-dimensional finite element osteonal model was prepared. Because locally the apatite follows the collagen orientation (Ascenzi A. et al., 1966), the apatite orientation was taken to equal the dominant collagen orientation observed in the confocal images. Perfect bonding of elementary components and continuity of tissue was assumed, with the exception of modeled osteocyte lacunae. The methodology used herein allows design of the osteon model to contain a lacunar distribution that is either user-assigned or automated to follow experimentally observed distributions. This new modeling method allows assignment of element-specific material properties that depend on the location of the element within the model, and modeled collagen-apatite orientation homogeneously within the element.

Maple software was employed as a pre-processor for the finite element software Abaqus. The thick cylindrical shell that models the osteon is divided into coaxial thin shells that model the lamellae containing the pseudo-ellipsoids that model the osteocyte lacunae. The parameters listed below can be chosen by the user or by algorithms from a database (Ascenzi M.-G. et al, 2004). Additional algorithms check compatibility of user choices.

radii and height of thick cylindrical shell
number and thickness of coaxial thin shells
number of ellipsoids
centers and axes of ellipsoids with $\theta_r = \theta_c = 0°$
size of brick elements outside ellipsoids
size of 3D region that models the perilacunar region
type of brick elements (linear or quadratic)
material properties of element within modeled extinct or bright osteon
loading mode (tension or compression along cylindrical axis)
magnitude of loading
number of steps for loading The element mean size was set between 3 to 4 μm outside the ellipsoids modeling the lacunae located in the middle portion of the cylindrical shell. The material properties of the proposed model's ECM were modeled as locally unidirectional fiber composite (Ascenzi M.-G., 1999), where the collagen fibrils represented the composite's matrix, following the material science terminology, and the carbonated apatite crystallites represented the fibers. The stiffness matrix relative to a specific collagen orientation followed the composite formulation with small displacements (Vinson, 1993) and used 40% density for the apatite contained in fully-calcified osteons and the material properties for collagen and apatite previously employed (Ascenzi M.-G., 1999). Because so-called extinct osteon shows in cross-section under circularly polarized light approximately 3% bright area in the vicinity of the canal, the collagen orientation of the extinct osteon model is specified by a 3% proportion applied to the percentage distributions of orientations longitudinal, oblique, and transverse for the lamellae that appear respectively bright and extinct.

For the assignment of the material properties to a specific element, Maple was programmed to compute the material properties in dependence on the location of the element. If the element was part of the modeled perilacunar region, the material properties were computed in terms of the locally perpendicular orientation of collagen to the lacuna-matrix interface observed experimentally in this study. If the element was not part of the modeled perilacunar region, the material properties were computed in terms of the orientation of collagen observed experimentally in Ascenzi M.-G. and Lomotsev (2006). Specifically, the program chooses an orientation for collagen within distributions on the order of [5%, 15%, 68%, 12%] for the extinct lamella, and of [20%, 35%, 5%, 35%] for the bright lamella, where the order of percentages in the square brackets corresponds to orientations respectively transverse, oblique at 45°, longitudinal, and oblique at −45°, with respect to the osteon axis.

For the computation of the material properties of an element in terms of collagen orientation within the element, a stiffness matrix was obtained as follows. First, a stiffness matrix $Q_h$ for the linear orthotropic material with respect to the osteon axis that models the single osteon as a whole was written in terms of the nine variables that define such material. Then values of the variables determined by elastic moduli, shear moduli and Poisson's ratios previously obtained through mechanical testing, were specified. Specifically, 11.6 GPa and 5.5 GPa were used for the respective longitudinal and transverse elastic moduli for extinct osteons under tension. For bright osteons under compression, 6.3 GPa was used for the longitudinal and transverse elastic moduli. 4 GPa was assigned to the shear modulus and 0.3 to the Poisson's ratio for both tension and compression modes (Ascenzi A. and Bonucci, 1967, 1968, 1972 and 1976; Ascenzi A. et al., 1997; Ascenzi M.-G. and Lomovtsev, 2006).

Second, a stiffness matrix $Q_f$ that represents the locally unidirectionally fibered material, transversely isotropic along the circumferential (axis 2) and longitudinal (axis 3) directions, was written in terms of five parameters of which some are known (see for instance Ascenzi, M-G, 1999). The unknown parameters of $Q_h$ and of $Q_f$ were then obtained by solving the system of equations resulting by equating the orthotropic matrix $Q_h$ with the matrix that averages radially the contributions of the conjugate matrices $(T_\gamma)^{-1} Q_f T_\gamma$ where $T\gamma$ is the rotation matrix around the radial axis 1 relative to the collagen orientation defined by the angle $\gamma$ (see for instance Vinson, 1993) that varies along the distributions observed inside and outside the perilacunar region. By so doing, the material properties assigned to the elements of the osteon model by means of the matrix $(T_\gamma)^{-1} Q_f T_\gamma$, in combination, yield overall the homogeneous material properties observed for single osteons. For the extinct osteon under tension, the 21 [i, j] entries of the symmetric matrix $(T_\gamma)^{-1} Q_f T_\gamma$ are [1,1]= 6.59; [1,2]=−0.33 $\cos(\gamma)^2$+2.68; [2,2]=6.43 $\cos(\gamma)^4$−13.05 $\cos(\gamma)^2$+13.21; [1,3]=0.33 $\cos(\gamma)^2$+2.36; [2,3]=2.68; [3,3]=6.43 $\cos(\gamma)^4$+0.19 $\cos(\gamma)^2$+6.59; [1,4]=0.33 $\sin(\gamma)\cos(\gamma)$; [2,4]=−6.43 $\sin(\gamma)\cos(\gamma)^3$+6.52 $\sin(\gamma)\cos(\gamma)$; [3,4]=6.43 $\sin(\gamma)\cos(\gamma)^3$+0.09 $\sin(\gamma)\cos(\gamma)$; [4,4]=−12.86 $\cos(\gamma)^4$+12.86 $\cos(\gamma)^2$+4; [1,5]=0; [2,5]=0; [3,5]=0; [4,5]=0; [5,5]=1.88 $\cos(\gamma)^2$+2.12; [1,6]=0; [2,6]=0; [3,6]=0; [4,6]=0; [5,6]=1.88 $\sin(\gamma)\cos(\gamma)$; [6,6]=−1.88 $\cos(\gamma)^2$+4. For the bright osteon under compression, the entries are [1,1]=8.48; [1,2]=1.73 $\cos(\gamma)^2$ $10^{-5}$+3.63; [2,2]=1.69 $\cos(\gamma)^4$−1.69 $\cos(\gamma)^2$+8.48; [1,3]=−1.73 $10^{-5}$ $\cos(\gamma)^2$+3.63; [2,3]=−1.69 $\cos(\gamma)^4$+1.69 $\cos(\gamma)^2$+3.63; [3,3]=1.69 $\cos(\gamma)^4$+1.69 $\cos(\gamma)^2$+8.48; [1,4]=−1.73 $10^{-5}$ $\sin(\gamma)$ $\cos(\gamma)$; [2,4]=−1.70 $\sin(\gamma)\cos(\gamma)^3$+0.84 $\sin(\gamma)\cos(\gamma)$; [3,4]=1.70 $\sin(\gamma)\cos(\gamma)^3$−0.84 $\sin(\gamma)\cos(\gamma)$; [4,4]=4; [1,5]=0; [2,5]=0; [3,5]=0; [4,5]=0; [5,5]=1.58 $\cos(\gamma)^2$+2.42; [1,6]=0; [2,6]=0; [3,6]=0; [4,6]=0; [5,6]=1.58 $\sin(\gamma)\cos(\gamma)$; [6,6]=−1.58 $\cos(\gamma)^2$+4.

The nodes on one base of the model were constrained on the plane perpendicular to the axis of the hollow cylinder that models the osteon (FIG. 6b). On the other base, defined as a surface of the adjacent elements, loading was applied as a uniform distribution (FIG. 6b). Two steps simulated the quasi-static application of two 5 g weights to the extensometer used under either tension or compression within the elastic range.

Maple was programmed to produce text files as input for Abaqus. Maple produces the input files within a few minutes on a personal computer to include 70 ellipsoids that model lacunae. With quadratic 20-node elements of 3 µm mean size, Abaqus runs for five days (4.23093×10$^5$ sec of CPU time; 35.15 gbytes of memory used for each loading step) on supercomputer Datastar (Teragrid, UC San Diego) to complete the analysis. The time necessary to complete the analysis decreased to two days when linear 8-node elements are used. However, the shape of the modeled lacuna yielded by the linear 8-node element model that uses straight segments as element edges is inferior relative to that associated with the quadratic polynomials allowed for by the quadratic 20-node elements. Indeed, the quadratic 20-node elements lacunar model more closely resembles the pseudo-ellipsoidal shape because an ellipsoidal surface is obtained by a quadratic equation. Elements of roughly constant size were employed throughout the thick cylindrical shell to allow for distributions of ellipsoidal placement that can extend to the entire thick shell.

Results:

The orientation of collagen bundles exiting the osteocyte lacuna (at the perilacunar region) is non-random and follows the specific patterns here described. The collagen bundles are observed to start at the lacunar wall, locally adjacent to the canaliculi with which they share a 360° distribution (FIG. 7). For the lacunae in extinct lamellar specimens, 72% of observed collagen in the proximal region; 72% of observed collagen in the distal; 81% of the observed collagen on the lateral left, and 79% of collagen at the lateral right, followed the adjacent canalicular orientation (Table I). For the lacunae in bright lamellar specimens, 72% of collagen in the proximal region, 71% of the collagen in the distal region, 80% of collagen in each of the lateral left and right regions, followed the adjacent canalicular orientation. That is, for the mentioned percentages for each of the lamellar types, the collagen follows locally at the perilacunar region the canalicular orientation, which is circumambiently perpendicular to the lacunar/ECM interface.

In Tables I and II, the percentages of lacunar images for which the collagen orientation that follows the adjacent canaliculum are listed by region (P for proximal, D for distal, Ll for lateral left, Lr for lateral right) with percentage means in bold for each of the 16 extinct lamellar specimens and each of the 16 bright lamellar specimens. Also, the number of images (#Im) and the absolute value of the angles that measure the tilt from the osteon axis $|\theta_r|$ and $|\theta_c|$ are provided. The means and standard deviations are listed in bold and the totals in italics.

TABLE I

| Spec # | % P | % D | % Ll | % Lr | #Im | $|\theta_r|$ | $|\theta_c|$ |
|---|---|---|---|---|---|---|---|
| e1 | 60 | 75 | 100 | 89 | 2 | 2.6 | 9.6 |
| e2 | 71 | 43 | 86 | 69 | 7 | 16.3 | 2.5 |
| e3 | 67 | 100 | 100 | 75 | 1 | 2.9 | 6.5 |
| e4 | 68 | 64 | 79 | 91 | 9 | 24.2 | 1.2 |
| e5 | 78 | 78 | 57 | 75 | 4 | 9.5 | 10.1 |
| e6 | 88 | 88 | 91 | 86 | 3 | 7.8 | 3.2 |
| e7 | 63 | 80 | 83 | 73 | 3 | 6.6 | 4.2 |
| e8 | 60 | 92 | 81 | 65 | 5 | 7.1 | 5.2 |
| e9 | 72 | 68 | 87 | 83 | 7 | 19.3 | 3.5 |
| e10 | 73 | 64 | 88 | 83 | 6 | 10.6 | 8.4 |
| e11 | 78 | 75 | 82 | 79 | 3 | 4.5 | 9.2 |
| e12 | 83 | 91 | 75 | 82 | 5 | 7.9 | 6.4 |
| e13 | 83 | 80 | 80 | 90 | 5 | 7.9 | 7.4 |
| e14 | 85 | 81 | 69 | 59 | 6 | 8.5 | 5.2 |
| e15 | 59 | 56 | 79 | 86 | 7 | 9.9 | 2.8 |
| e16 | 71 | 75 | 75 | 83 | 3 | 4.1 | 3.8 |
| Means | 72 | 72 | 81 | 79 | | 9.4 ± 5.9 | 5.6 ± 2.8 |
| *Totals* | *79* | *80* | *81* | *79* | *76* | | |
| b1 | 100 | 100 | 73 | 86 | 4 | 5.7 | 44.3 |
| b2 | 100 | 75 | 80 | 71 | 4 | 8.8 | 20.2 |
| b3 | 88 | 56 | 83 | 89 | 8 | 12.5 | 21.3 |
| b4 | 75 | 75 | 71 | 75 | 2 | 0.0 | 17.2 |
| b5 | 83 | 80 | 83 | 78 | 2 | 3.6 | 8.2 |
| b6 | 67 | 100 | 67 | 700 | 1 | 1.7 | 4.5 |
| b7 | 17 | 29 | 86 | 76 | 4 | 7.6 | 7.4 |
| b8 | 33 | 58 | 83 | 81 | 4 | 6.0 | 3.7 |
| b9 | 55 | 55 | 82 | 68 | 4 | 5.4 | 4.7 |
| b10 | 62 | 83 | 80 | 83 | 5 | 7.9 | 14.6 |
| b11 | 75 | 88 | 76 | 71 | 6 | 10.0 | 5.3 |
| b12 | 83 | 80 | 78 | 63 | 2 | 4.1 | 7.3 |
| b13 | 63 | 75 | 71 | 77 | 3 | 5.4 | 8.4 |
| b14 | 83 | 86 | 78 | 88 | 2 | 3.2 | 8.3 |
| b15 | 86 | 75 | 86 | 77 | 3 | 4.3 | 6.4 |
| b16 | 75 | 71 | 80 | 92 | 3 | 4.3 | 7.2 |
| Means | 72 | 71 | 80 | 80 | | 5.7 ± 3.2 | 11.8 ± 10.3 |
| *Totals* | *82* | *78* | *77* | *80* | *57* | | |

TABLE II

| Spec Type | Spec # | #y P | #n P | #y D | #n D | #y Ll | #n Ll | #y Lr | #n Lr |
|---|---|---|---|---|---|---|---|---|---|
| e | 1 | 3 | 2 | 3 | 1 | 9 | 0 | 8 | 1 |
| e | 2 | 18 | 3 | 12 | 9 | 25 | 4 | 22 | 10 |
| e | 3 | 2 | 1 | 2 | 0 | 3 | 0 | 3 | 1 |
| e | 4 | 22 | 6 | 12 | 2 | 31 | 8 | 39 | 4 |
| e | 5 | 7 | 2 | 7 | 2 | 8 | 6 | 12 | 4 |
| e | 6 | 7 | 1 | 7 | 1 | 10 | 1 | 12 | 2 |
| e | 7 | 5 | 3 | 4 | 1 | 10 | 2 | 11 | 4 |

TABLE II-continued

| Spec Type | Spec # | #y P | #n P | #y D | #n D | #y L1 | #n L1 | #y Lr | #n Lr |
|---|---|---|---|---|---|---|---|---|---|
| e | 8 | 9 | 6 | 12 | 1 | 17 | 4 | 13 | 7 |
| e | 9 | 16 | 2 | 16 | 3 | 26 | 4 | 25 | 5 |
| e | 10 | 15 | 1 | 12 | 2 | 22 | 3 | 20 | 4 |
| e | 11 | 7 | 2 | 6 | 2 | 9 | 2 | 11 | 3 |
| e | 12 | 10 | 2 | 10 | 1 | 15 | 5 | 18 | 4 |
| e | 13 | 10 | 2 | 8 | 2 | 16 | 4 | 19 | 2 |
| e | 14 | 11 | 2 | 13 | 3 | 20 | 9 | 16 | 11 |
| e | 15 | 12 | 5 | 7 | 2 | 23 | 6 | 24 | 4 |
| e | 16 | 5 | 2 | 6 | 2 | 9 | 3 | 10 | 2 |
| Totals | | 76 | 159 | 42 | 137 | 34 | 253 | 61 | 263 |
| b | 1 | 7 | 0 | 5 | 0 | 11 | 5 | 12 | 2 |
| b | 2 | 12 | 0 | 9 | 3 | 12 | 4 | 12 | 5 |
| b | 3 | 21 | 3 | 10 | 8 | 33 | 7 | 34 | 4 |
| b | 4 | 3 | 1 | 3 | 1 | 5 | 2 | 6 | 2 |
| b | 5 | 5 | 1 | 4 | 1 | 4 | 2 | 7 | 2 |
| b | 6 | 2 | 1 | 2 | 0 | 2 | 1 | 5 | 0 |
| b | 7 | 4 | 2 | 5 | 2 | 12 | 2 | 13 | 4 |
| b | 8 | 7 | 5 | 10 | 2 | 15 | 3 | 13 | 3 |
| b | 9 | 9 | 2 | 9 | 2 | 14 | 3 | 13 | 6 |
| b | 10 | 11 | 2 | 10 | 2 | 16 | 4 | 19 | 4 |
| b | 11 | 14 | 2 | 15 | 2 | 22 | 8 | 20 | 8 |
| b | 12 | 5 | 1 | 4 | 1 | 7 | 2 | 5 | 3 |
| b | 13 | 5 | 3 | 6 | 2 | 10 | 4 | 10 | 3 |
| b | 14 | 5 | 1 | 6 | 1 | 7 | 2 | 7 | 1 |
| b | 15 | 6 | 1 | 6 | 2 | 12 | 2 | 10 | 3 |
| b | 16 | 6 | 2 | 5 | 2 | 12 | 6 | 12 | 1 |
| Totals | | 122 | 27 | 109 | 31 | 194 | 57 | 198 | 51 |

The proximal and distal regions were differentiated in reference to a "sharp" and "round" appearance (FIG. 4a-4c). The 95% of lacunar images of extinct lamellae that showed a combination of one sharp apex and a second round apex (Table III) was significantly larger than the 44% of the lacunar images of bright lamellae that showed a combination of one sharp apex and a second round apex ($p<0.05$). The 50% of bright lamellar observations of lacuna with a sharp apex at which the collagen follows the adjacent canalicular orientation is statistically larger than the 43% of extinct lamellar observations that show a lacuna with a sharp apex at which the collagen follows the adjacent canalicular orientation ($p<0.05$).

Additionally, the proximal and distal perilacunar regions were investigated in reference to the lacunar tilt, radially and circumferentially (see absolute values of $\theta r$ and $\theta c$ in Table I). The lacunae are more likely to be tilted radially in extinct than in bright lamellae (9.4 vs. 5.7, $p=0.04$). The lacunae are less likely to be tilted circumferentially in extinct lamellae than in bright lamellae (5.6 vs. 11.8, $p=0.03$). The percentage of radially tilted lacunae with collagen following the adjacent canalicular orientation at the slender apex (FIGS. 3 and 4) is significantly smaller in extinct, than in bright, lamellae (43% vs. 50%, $p<0.05$).

In order to further investigate the role of osteocyte lacunae as micro-crack concentrators and/or initiators, a novel three-dimensional (3D) finite element osteonal modeling method was prepared. The osteon model is designed to contain a lacunar distribution that is either user-assigned or automated to follow experimentally observed distributions. Because each element of the mesh can be assigned a specific material property and the element size is small, this new modeling method allows simulation of collagen-apatite orientation with a resolution on the order of 27 $\mu m^3$.

The osteon model shows that at the equatorial region, defined as the middle transverse portion of the perilacular region, at the upper end of the elastic range under quasi-static tensional loading, the stress at the perilacunar region is on the order of $4.1 \times 10^{-3}$ GPa (FIGS. 8a and 8b), 42% reduced at the equatorial region in comparison to the stresses that would be generated by the collagen orientation distribution observed away from the lacuna (FIG. 8c) if it were located at the lacuna's equatorial region.

The extinct osteon model under elastic axial tension shows the maximum principal strain (FIGS. 8a and b) peaking at the perilacunar region, relative to the rest of the osteon model (mean 170 $\mu\epsilon$ vs. 132 $\mu\epsilon$, $p<0.01$). Specifically, the maximum values (FIG. 8c, 216 $\mu\epsilon$ for a representative lacuna) occur within the middle Transverse section (M in FIG. 8d) of the perilacunar equator (E in FIG. 8c), defined as the middle portion of the three-dimensional perilacunar region. The Mises stress is larger at the mid equatorial region than elsewhere in the perilacunar region ($1.22 \times 10^{-3}$ GPa vs. $1.10 \times 10^{-3}$ GPa, $p=0.01$). Within the equatorial region, the maximum Mises stress is reached at the mid-equatorial region ($1.31 \times 10^{-3}$ GPa vs $1.17 \times 10^{-3}$ GPa, $p<0.01$). FIG. 8f provides a sample of the angle $\gamma$ distribution that defines the fiber orientation of the composite (FIGS. 8a, b, e). Relative to a homogeneous model, at the equatorial region the strain is significantly larger (e.g., 205 $\mu\epsilon$ vs. 135 $\mu\epsilon$, $p<0.01$) and the stress is significantly smaller (e.g., $1.22 \times 10^{-3}$ vs. $1.55 \times 10^{-3}$ GPa, $p<0.01$) (FIGS. 8c, g, h, i).

The bright osteon model under elastic axial compression shows that the maximum principal strain (FIGS. 8j and k) peaks at the perilacunar region, relative to the rest of the osteon model (mean 93 $\mu\epsilon$ vs. 91 $\mu\epsilon$, $p<0.01$). Specifically, the maximum values (FIG. 8l, 99 $\mu\epsilon$ for a representative lacuna) occur within the equatorial region. The Mises stress is larger at the equator than in the remainder of the perilacunar region ($2.02 \times 10^{-3}$ GPa vs. $1.69 \times 10^{-3}$ GPa, $p<0.01$). The Mises stress is largest at the mid-equatorial region ($2.06 \times 10^{-3}$ GPa vs. $2.00 \times 10^{-3}$ GPa, $p=0.01$). Relative to the homogeneous model, at the equatorial region the strain is significantly larger (99 $\mu\epsilon$ vs. 92 $\mu\epsilon$, $p<0.01$), and the stress is significantly smaller ($2.02 \times 10^{-3}$ GPa vs. $1.88 \times 10^{-3}$ GPa, $p<0.01$) (FIGS. 8n-p).

Discussion

The novelty provided by the present invention is the biomechanical role of the orientation of collagen relative to the local canalicular orientation in secondary lamellae at the interface between osteocyte lacuna and ECM. Confocal microscopy was used to observe collagen in relation to presence of canaliculi and lacunae because of: (i) its higher resolution relative to polarized light microscopy and (ii) its capability to observe directly collagen orientation through sequential virtual slices, without gaps between slices, unlike X-ray diffraction and electron microscopy. The following section addresses results, biomechanical implications, and advances in modeling that are associated with this invention.

Experimental observations concerning the osteon's outermost lamella were also used elsewhere in the osteon in preparing the osteon model. Additionally, a high number of elements for FEA was used, but smaller elements at the interface between lacuna and ECM would increase adherence of material properties to observed circumambient orientation.

The collagen orientation at the perilacunar region away from the lacunar apices showed a general circumambiently perpendicular orientation that matched the canalicular orientation (FIG. 9a). Such distribution is independent from the lamellar type, extinct or bright. The lamellar type, extinct or bright, may imply a characteristic range of tilt of the osteocyte lacuna with respect to the osteon axis. Because an extinct lamella appears thicker than a bright lamella in cross-section under circularly polarized light and confocal microscopy, it would be able to contain a lacuna with a larger radial tilt than would a bright lamella. A lacuna with a smaller circumferential tilt in the extinct lamella and with a larger circumferential tilt in the bright lamella would follow the dominant orientation of collagen away from the perilacunar region (Ascenzi et al., 2003; Ascenzi and Lomovtsev, 2006). Interestingly, the observed magnitude of the lacunar radial tilt is on the order of the angle observed for the Haversian system (Petrtýl et al., 1996).

For both lamellar types, the finite element model of predominantly extinct osteon with lacunae whose major axis parallels the osteon axis, indicated that the equatorial region of the lacuna-ECM interface is the region with the highest stresses (FIG. 8). Such region is located perpendicularly to the direction of loading and at the greatest distance from the lacunar axis. It therefore undergoes the greatest displacement as the lacunar space within progressively reduces transversely to the axial loading. The extent of the deformation depends on the radial distance from the canal, on the order of $7.8 \times 10^{-3}$ μm per unit length for a lacuna located at two-thirds of the osteon thickness. At the equatorial region, the collagen/apatite elements running transversely to the osteon axis may very well be prestressed in compression (Ascenzi M.-G., 1999; Ascenzi M.-G. et al., 2000) further delaying microcrack formation in the ECM during tension. The circumambiently perpendicular orientation of collagen at the equatorial section of the lacuna is therefore may reinforce the ECM to better resist the stress generated under tensional loading.

The results relative to the equatorial region of the osteocyte lacuna are compatible with observations by confocal microscopy of micro-cracks (under a loading higher than modeled here) propagating normally to the direction of loading and perpendicular to long axis of lacunae (Reilly, 2000). Indeed, the occurrence of the foregoing corresponds to the observed parallelism between collagen orientation and the micro-cracks forming within the interfibrillar substance, among the collagen fibrils, parallel to the fibrils' length, observed by transmission electron microscopy in human osteons (Ascenzi A. and Bonucci, 1976).

Currey (2003) hypothesized that the orientation of the osteocyte lacuna and the "flow" of lamellae around the osteocyte lacuna minimize their stress-concentrating effect while the elastic anisotropy of bone may enhance it. However, the osteocyte lacuna is more likely to be tilted off the circumferential-axial reference (FIG. 1b) in the extinct lamella than in the bright lamella. Either the sharp or the round apex of the lacuna is less likely to show the collagen following the adjacent canalicular orientation in the extinct lamella than in the bright lamella. The osteocyte lacunae within the extinct lamella can show a tilt that augments the radial extent of the lacuna, because the extinct lamella reveals itself as thicker than bright lamellae in cross-section under circularly polarized light. Further, the bright lamella is more likely to show collagen following the canalicular orientation at either the sharp or round apex in order to reinforce the tissue. In fact, the structure of the bright lamella is more likely than extinct lamella's structure to undergo fracture, because of its collagen orientation distribution that forms larger acute angles and shows more collagen transverse to the osteon axis than elsewhere in the lamella (Ascenzi M.-G. et al., 2000 and 2003; Ascenzi M.-G. and Lomovtsev, 2006).

With the confocal microscopy employed here on the isolated lamellar specimens, $\theta_r$ cannot be measured (FIG. 3) because the axis of the microscope parallels the radial direction. Such value is indicated as small (Ascenzi M.-G. et al., 2004). Nevertheless, the appearance of the lacunar apices, one sharp and one round, is interpreted as a non-zero value of $\theta_r$ and is the subject of the results according to the present invention. A non-zero value of $\theta_r$ is more likely to occur (95% vs. 44%) on extinct lamella than bright lamella. Nevertheless, the collagen that parallels the canaliculus at the sharp apex, which more likely would elongate by cracking, in the bright lamella may actually protect the lacuna from fracture. On the lamellar specimens observed, the osteocyte lacuna forms an angle $\theta_c$ (FIG. 3) up to 7° with respect to the osteon axis in the extinct lamellae and as large as 49° in the bright lamellae. Because the dominant orientation distribution of collagen in the lamella away from the lacuna forms small angles with the osteon axis for extinct lamella on the same circumferential-longitudinal reference away from the lacuna and larger angles for the bright lamella, such values of the angle $\theta_c$ appear to follow the dominant orientation distribution of collagen in the lamella away from the lacuna. The osteon model of the present invention refers to lacunae with null $\theta_c$.

Since classification of bone's hierarchical structure (Petersen, 1930), secondary osteons have been viewed as composite reinforced with either fibers (Gebhardt, 1906; Currey, 1964, 1969; Ascenzi A. and Bonucci, 1976; Katz, 1981; Giraud-Guille, 1988; Hogan, 1992; Pidaparti and Burr, 1992; Aoubiza et al., 1996) or platelets (Wagner and Weiner, 1992; Akiva et al., 1998; Weiner et al., 1999; Kotha and Guzelsu, 2002). The models developed from an orthogonal plywood to a multidirectional structure indicative of the osteon's adaptability to form under a variety of loading specifications and of the effective response to a wide range of mechanical stimulations. The assessment of strains and stresses at the pericular lacunar in relation to formation of microdamage (Piekarski, 1970) and formulation of hypotheses on the participation of osteocyte to mechano-transduction have brought to the development of two-dimensional finite element models that include lamellae (Prendergast and Huiskes, 1996) and 3D models of the perilacular region that include canaliculi exiting the lacuna (Bonivtch et al., 2007). The mechanical properties given to the elements had not taken into account the circumambient orientation of the collagen/apatite at the lacunar/ECM interface. Nevertheless, the model of the present invention shows amplification of ECM strains at the pericular regions consistent to the two previous models (Prendergast and Huiskes, 1996; Bonivtch et al., 2007) with the difference in the attenuation of stresses at the sites of highest strain. The circumambient orientation of the collagen/apatite at the lacunar/ECM interface would allow for the presence of higher strains while delaying the osteocyte lacuna from damage. Indeed, the moment micro-cracks start forming at the lacuna, the pericular region will be less effective as a stress concentrator.

Previous models of perilacunar region use material properties not correlated with collagen-apatite orientation (Prendergast and Huiskes, 1996; Nicolella et al., 2006; Bonivtch et al., 2007) and refer to a wider range of strain that exceeds the elastic range. In the comparison of stress magnitude, the present invention considers much smaller stresses as a way to initially separate the elastic and inelastic ranges to study both separately.

Figure 9:
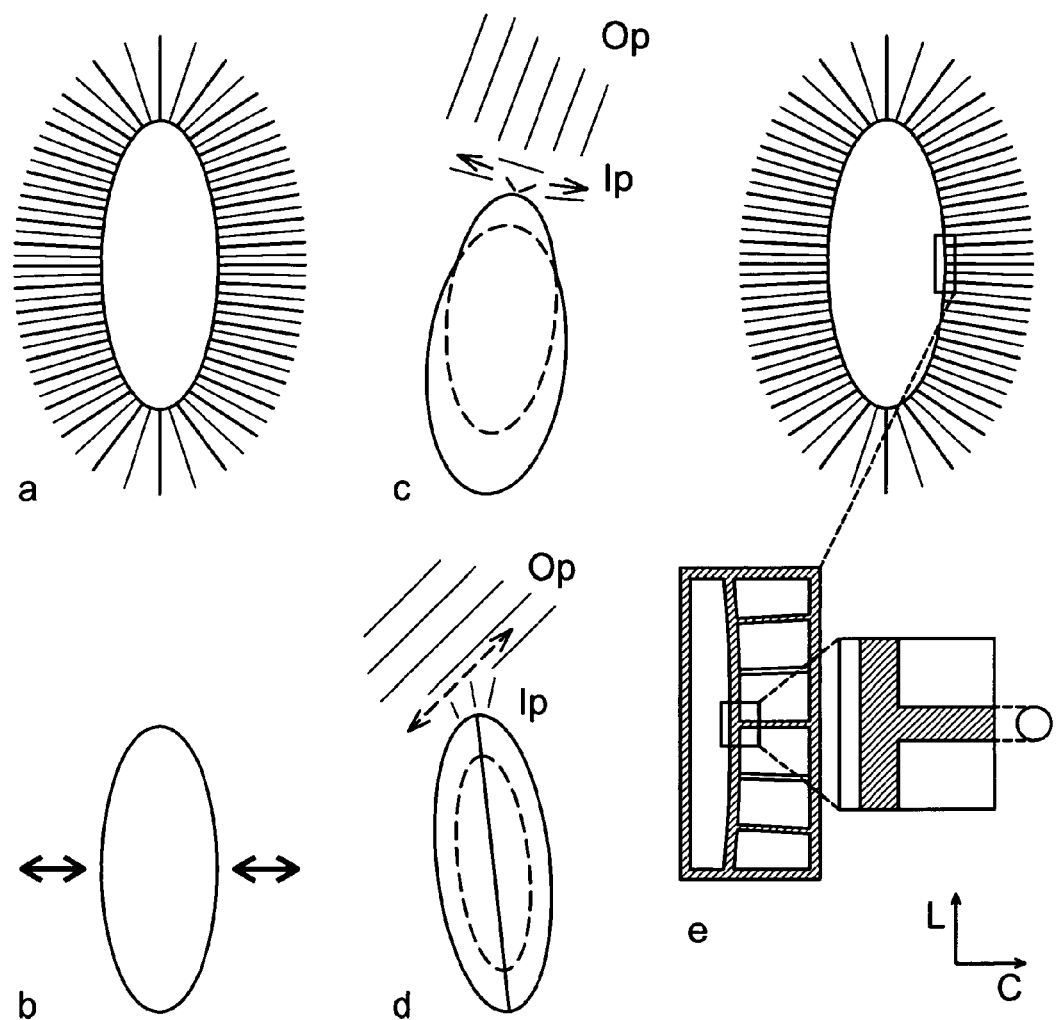
FIG. 9. (a) This is a new model of collagen distribution (lighter grey) with respect to canalicular distribution (darker grey) at the perilacunar region. (b) Both under tension and compression, the generally circumambiently-perpendicular orientation of collagen-apatite at the perilacunar region, parallels the direction of the greatest deformation at the equatorial region. (c) In the extinct lamella, the higher chance that the lacuna is tilted radially (depicted by the eccentric ellipses) and the lesser likelihood that the collagen follows the canaliculi at the apex, may facilitate deflection of a micro-crack. (d) In the bright lamella, a micro-crack would be deflected because of the high percentages of collagen-apatite orientation forming a wide angle (±45°) with the axial direction. (e) The effect of the canalicular presence is stronger at the interface with the lacuna and maximum (vertical line in left rectangle) at the radial mid-lacuna equator (in square). The detail in the square is enlarged and rotated to show the canalicular section.

According to the present invention, the collagen orientation at the perilacunar region is circumambiently perpendicular to the lacuna (FIG. 9). Consequently, the osteon model of the present invention not only utilizes data and information on the orientation of collagen/apatite away from the lacunae (Ascenzi M.-G. and Lomovtsev, 2006), but also utilizes data and information on the collagen and apatite orientation near the lacuna (i.e., in the perilacunar region). Thus, the osteon model of the present invention includes distribution of osteocyte lacunae within the osteon that follows additional experimentally observed biological variations (Ascenzi M.-G. et al., 2004). Such a model is a beneficial and helpful tool in characterizing and predicting fracture initiation, propagation, and arrest.

Further, micro-cracks' initiation and propagation under axial loading may be associated with collagen-apatite orientation. The micro-cracks' propagation at mid-lacuna previously observed (Reilly, 2000) agrees with the collagen orientation observed here because the collagen is oriented perpendicularly to the lacunar major axis at the mid-lacuna (FIG. 9b). Indeed, the foregoing corresponds to the observed parallelism between collagen orientation and micro-cracks' formation within the interfibrillar substance (Ascenzi and Bonucci, 1976).

Micro-cracks' initiation at the lacunar apices under axial loading may be associated with the tilt of the osteocyte lacuna, in conjunction with collagen-apatite orientation. Indeed, the fracture toughness at a lacunar apex depends on the angle between the major axis of the lacuna and the osteon axis, and on the grain of the surrounding tissue (Martin et al., 1998). Because a lacuna in the extinct lamella is more likely to be tilted radially than in the bright lamella, a micro-crack would more likely form at the lacunar apex. The lesser likelihood that the collagen follows the canaliculi at the apex may help promptly to deflect the micro-crack that would otherwise propagate generally longitudinally, thereby reducing chances of further propagation (FIG. 9c). Differently in the bright lamella (FIG. 9d), a micro-crack, likely to start at a lacunar apex because locally at the apex the collagen follows the canaliculi, would turn away from the osteon axis, because of the high percentages of collagen orientation forming a wide angle (on the order of ±45°) with respect to the osteon axis.

Secondary osteon models have developed towards a multidirectional structure, which reflects the osteon's ability to function and remodel under a variety of loading specifications (Gebhardt, 1906; Currey, 1964, 1969; Ascenzi and Bonucci, 1976; Katz, 1981; Giraud-Guille, 1988; Hogan, 1992; Pidaparti and Burr, 1992; Wagner and Weiner, 1992; Aoubiza et al., 1996; Akiva et al., 1998; Weiner et al., 1999; Jäger and Fratzl, 2000; Cowin, 2001; Kotha and Guzelsu, 2002; Jasiuk and Ostoja-Starzewski, 2004). The angle between the elementary components' orientation and the loading direction was observed to affect strain and stress fields. The "lacuna-enhanced osteon" model of the present invention displays the axial deformation observed experimentally (Ascenzi and Bonucci, 1967, 1968; Ascenzi et al., 1985, 1997). The mesh density was established through a convergence study on an increasing number of nodes, from 58,100 to 1,917,873. The difference in computed maximum principal strain was found to be 1.6%, smaller than the 2% required (Zienkiewicz and Taylor, 1989) at the last step of the study. The osteon model of the present invention is meshed with 20-node elements of mean size 3 µm, on the order of 464,800 elements and 1,917,873 distinct nodes, determined by osteon dimensions and lacunar number.

Figure 6:
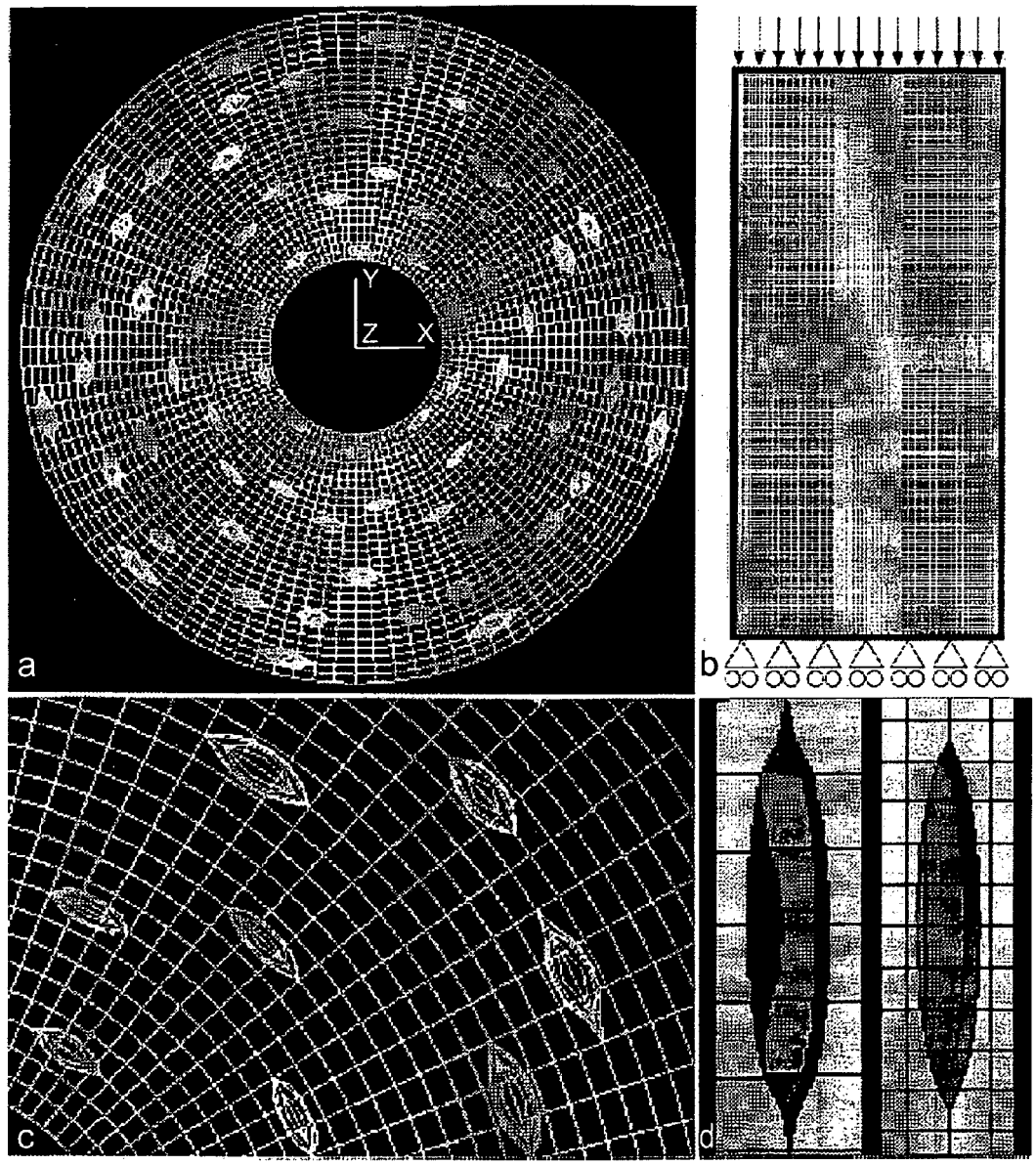
FIG. 6. Meshing represents finite elements in images (a) through (e). (a) This is the transverse wire frame view of a 498 µm-long osteon model with radii measuring 30 and 114 µm, used for simulation of tensional loading. Seventy osteocyte lacunae are represented by an automated distribution. Elements measure 3 µm in radial and longitudinal out-of-plane length and from 1.88 to 9.11 µm in circumferential length that increases with the radius. (b) This circumferential-longitudinal wireframe view of the osteon model shows the axial load distribution (arrows) at the upper base that can occur either in tension or compression, the boundary conditions at the lower base constrained along the osteon axis and the positioning of the modeled osteocyte lacunae within a 42 µm-long portion of the thick cylinder whose midsection is viewed in (a). (c) This detail of the osteon model shows eight lacunar models on a transverse section. (d) These examples of longitudinal sections of lacunar models show the lateral perilacunar elements through the empty lacunae.

The strain concentration role of lacunae is evidenced by the simulations of osteon with lacunae, whose major axis parallels the osteon axis (FIGS. 6 and 8). Indeed, a 2.1 average concentration factor, defined as the ratio between strain at the perilacunar region and the axial strain applied to the osteon, is found for the extinct osteon under elastic tension, and a smaller average concentration factor of 1.3 is found for the bright osteon under elastic compression. A larger perilacunar region had no effect on the local mechanical response, in agreement with Bonivtch et al. (2007). Further, the concentration factor (1.1-3.8) measured by Nicolella et al. (2006) on bovine bone at higher strains, brackets the instant values.

The mid-equatorial region is the site with the highest strains under either tension or compression (FIG. 8). It is located at the greatest distance from the lacunar axis. It therefore undergoes the greatest displacement as the lacunar space progressively decreases under tension, and enlarges under compression. The orientation of collagen at the mid-equator (FIG. 9a) may reinforce the ECM to better resist the stress generated under tensional loading (FIG. 9b). The lacuna-enhanced osteon model of the present invention, the first to include the collagen-apatite orientation, shows amplification of perilacunar strains consistent with the two-dimensional osteon model with lacunae (Prendergast and Huiskes, 1996) and the three-dimensional "boxed" model of a perilacunar region of one lacuna with 10 canaliculi (Bonivtch et al., 2007).

On the basis of the simulation in progress of a lacuna-enhanced osteon model with 1 µm-diameter diameter canaliculi, it is observed that the canalicular presence affects mostly the lacunar wall at the somewhat circular canalicular section under axial tension (FIG. 9e; McCreadie and Hollister, 1997). The strain that was already maximum at mid-equator without canalicular consideration, increased by 9% (with a corresponding 10% stress increase) with the canalicular presence. Under the simplifying use of homogeneous material properties, the 87% strain increase (with a 10% stress increase) is consistent with the 97% strain increase in Bonivtch et al. (2007).

In conclusion, the new collagen orientation distribution at the perilacunar region according to the present invention is generally circumambiently-perpendicular to the lacuna and follows the canalicular orientation at the lateral perilacunar region. At the lacunar apices, the collagen distribution differs according to lamellar type, extinct or bright. Its role away from the apices may be linked to the deformation at the equatorial region under tensional and compressive loading. The stress attenuation at the sites of highest strain would function to delay occurrence of damage.

BIBLIOGRAPHY

Akiva, U., Wagner, H. D., Weiner, S., 1998. Modeling the three-dimensional elastic constants of parallel-fibred and lamellar bone. Journal of Material Science. 33, 1497-1509.

Amprino, R., and Engström, A., 1952. Studies on X-ray absorption and diffraction of bone tissue. Acta Anatomica. 15, 1-22.

Aoubiza, B., Crolet, J. M., Meunier, A., 1996. On the mechanical characterization of compact bone structure using homogenization theory. Journal of Biomechanics 29, 1539-1547.

Ascenzi, A. and Bonucci, E., 1967. The tensile properties of single osteons. The Anatomical Record 158, 375-386.

Ascenzi, A., Bonucci, E. 1968. The compressive properties of single osteons. The Anatomical Record 161, 377-391.

Ascenzi, A. and Bonucci, E., 1972. The shearing properties of single osteons. The Anatomical Record 172, 499-510.

Ascenzi, A. and Bonucci, E., 1976. Mechanical similarities between alternate osteons and cross-ply laminates. J. Biomech. 9, 65-71.

Ascenzi, A., Ascenzi M.-G., Benvenuti, A., Mango, F. and Simili, R., 1985. Mechanical hysteresis loops for single osteons: technical devices and preliminary results. J. Biomech., 18, 391-398.

Ascenzi, A., Ascenzi, M.-G., Benvenuti, A., Mango, F., 1997. Pinching in longitudinal and alternate osteons during cyclic loading. J. Biomech., 30, 689-676.

Ascenzi, A., Benvenuti, A., Mango, F., Simili, R., 1985 Mechanical hysteresis loops from single osteons: technical devices and preliminary results. J. Biomech. 18, 391-398.

Ascenzi, A., Bonucci, E. and Bocciarelli, D. S., 1966. An electron microscope study on primary periosteal bone. Journal of Ultractural Research 18, 605-618.

Ascenzi, M.-G. and Lomovtsev, A., 2006. Collagen orientation patterns in human secondary osteons, quantified in the radial direction by confocal microscopy. Journal of Structural Biology 153, 14-30.

Ascenzi, M.-G. and Lomovtsev, A., 2008. Orientation of collagen at the osteocyte lacunae in human secondary osteons. J. Biomech. 41(16):3426-35.

Ascenzi, M.-G., 1999. A first estimation of prestress in so-called circularly fibered osteonic lamellae. J. Biomech. 32, 935-942.

Ascenzi, M.-G., Andreuzzi, M. and Kabo, J. M., 2004. Mathematical modeling of secondary osteons. Scanning 26, 25-35.

Ascenzi, M.-G., Ascenzi A., Burghammer M., Panzavolta S., Benvenuti A., Bigi A., 2003. Structural differences between "dark" and "bright" isolated human osteonic lamellae. Journal of Structural Biology 141, 22-33.

Ascenzi, M.-G., Benvenuti, A., and Ascenzi, A. (2000) Single osteon micromechanical testing. In: An, Y., Draughn, R. (Eds.), Mechanical Testing of Bone (An Y. and Draughn R. Eds.). pp. 271-290, CRC Press, Boca Raton, Fla.

Atkinson, P. J. and Hallsworth, A. S., 1982. The special structure of bone. I, in: Harrison, R. J. and Navaratman, V. (Eds.), Progress in Anatomy, Cambridge University Press, Great Britain, Vol. 2, pp. 179-199.

Bonivtch, A. R., Bonewald, L. F., and Nicolella, D. P., 2007. Tissue strain amplification at the osteocyte lacuna: a microstructural finite element analysis. J. Biomech., 40, 2199-2206.

Cowin, S. C., 2001. Bone Mechanics Handbook. CRC Press, Boca Raton.

Currey, J., 1962. Stress concentration in bone. Quarterly Journal of Microscopy Science, 103, 111-133.

Currey, J., 1964. Three analogies to explain the mechanical properties of bone. Biorheology 2, 1-10.

Currey, J., 1969. The relationship between the stiffness and the mineral content of bone. J. Biomech. 2, 477-480.

Currey, J. 2003. The many adaptations of bone. J. Biomech. 36, 1487-1495.

Enlow, D. H., 1962. Functions of haversian systems. American J. Anat. 110, 269-305.

Gebhardt, W., 1906. Ueber funktionell wichtige Anordnungsweisen der feineren und gröberen Bauelemente des Wirbeltierknochens. II. Spezieller Teil. 1. Der Bau der Haverssohen Lamellensysteme und seine funktionelle Bedeutung. Archiv für Entwicklungsmechanik der Organismen. 20, 187-322.

Giraud-Guille, M.-M., 1988. Twisted plywood architecture of collagen fibrils in human compact bone osteons. Calcified Tissue International. Tissue Int. 42, 167-180.

Hogan, H. A, 1992. Micromechanics modeling of Haversian cortical bone properties. J. Biomech. 25, 549-556.

Jäger, I. and Fratzl, P., 2000, Mineralized collagen fibrils: A mechanical model with staggered arrangement of mineral particles. Biophysics Journal. 79, 1737-1746.

Jasiuk, I., and Ostoja-Starzewski, M., 2004. Modeling of bone at single lamella level. Biomechanics and Modeling in Mechanobiology 3, 67-74.

Katz, J. L., 1981. Composite material models for cortical bone, in: Cowin, S. C. (Ed.), Mechanical Properties of Bone, American Society of Mechanical Engineers, New York, AMD, Vol. 45, pp. 171-184.

Kotha, S. P. and Guzelsu, N., 2002. Modeling the tensile mechanical behavior of bone along the longitudinal direction. J. Theor. Biol. 219, 269-79.

Leeuwenhoek, A. (v), 1693. An extract of a letter from Mr. Anth. Van. Leeuwenhoek, containing several observations on the texture of the bones of animals compared with that of wood: on the bark of trees: on the little scales found on the cuticula, etc. Philos. Trans. R. Soc. London 202, 838-843.

Marotti, G., 1979. Osteocyte orientation in human lamellar bone and its relevance to the morphometry of periosteocytic lacunae. Metabolic Bone Dis. & Rel. Res. 1, 325-333.

Martin, R. B., Burr, D. B., Sharkey, N. A., 1998. Skeletal Tissue Mechanics. Springer, N.Y.

McCreadie, B. R., Hollister, S. J., 1997. Strain concentrations surrounding an ellipsoidal model of lacunae and osteocytes. Computer Methods in Biomechanics and Biomedical Engineering 1, 61-68.

McNamara, L. M., Van der Linden, J. C., Weinans, H., and Prendergast, P. J., 2006. Stress-concentrating effect of resorption lacunae in trabecular bone. J. Biomech. 39, 734-741.

Mohsin, S., O'Brien, F. J., Lee, T. C., 2006. Osteonal crack barriers in ovine compact bone. Journal of Anatomy. 208, 81-89.

Nicolella, D. P., Moravits, D. E., Gale, A. M., Bonewald, L. F., Lankford J., 2006. Osteocyte lacunae tissue strain in cortical bone. J. Biomech. 39, 1735-1743.

O'Brien, F. J., Hardiman, D. A., Hazenberg, J. G., Mercy, M. V., Mohsin, S., Taylor, D., Lee, T. C., 2005b. The behavior of microcracks in compact bone. Eur. J. Morph. 42, 71-79.

O'Brien, F. J., Taylor, D., and Lee, T. C., 2005a. The effect of bone microstructure on the initiation and growth and microcracks. J. Orth. Res. 23, 475-480.

Petersen, H., 1930. Die Organe des Skeletsystems. I, in Möllengorff (v.), W. (Ed.) Handbuch der mikroskopischen Anatomie des Menschen, Springer, Berlin, Vol. 2, Part 2, pp. 521-678.

Petrtýl, M., Hert, J., Fiala, P., 1996 Spatial organization of the haversian bone in man. J. Biomech. 29, 161-169.

Pidaparti, R. M. V. and Burr, D. B., 1992. Collagen fiber orientation and geometry effects on the mechanical properties of secondary osteons. J. Biomech. 25, 869-880.

Piekarski K., 1970. Fracture of bone, J. Appl. Physiol. 41, 215-223.

Prendergast, P. J., and Huiskes, H. W. J. 1996. Microdamage and osteocyte-lacuna strain in bone: A microstructural finite element analysis J. Biomech. Eng., Trans. ASME, 118, 240-246.

Reilly, G. C., 2000. Observation of microdamage around osteocyte lacunae in bone. J. Biomech. 33, 1131-1134.

Simkin, A. and Robin G., 1974. Fracture formation in differing collagen fiber pattern in compact bone. J. Biomech. 7, 183-188.

Skedros, J. G., Grunander, T. R., and Hamrick, M. W., 2005. Spatial distribution of osteocyte lacunae in equine radii and third metacarpals: Considerations for cellular communication, microdamage detection and metabolism. Cells Tissues Organs. 180, 215-236.

Vinson, J. R., 1993. The Behavior of Shells Composed of Isotropic and Composite Materials. Kluwer Academic Publishers, Dordrecht, The Netherlands.

Wagner, H. D. and Weiner, S., 1992. On the relationship between the microstructure of bone and its mechanical stiffness. J. Biomech. 25, 1311-1320.

Weiner, S., Traub, W., Wagner, H. D., 1999, Lamellar bone: structure-function relations. J. Struct. Biol. 126, 241-255.

Zienkiewicz, O. C., Taylor, R. L., 1989. The Finite Element Method. McGraw-Hill, New York.

All references cited and/or discussed in this specification are incorporated herein by reference in their entireties and to the same extent as if each reference was individually incorporated by reference.

What is claimed is:

1. A method of predicting a mechanical response of a subject bone osteon to an applied force comprising the steps of:
   (a) identifying a subject bone osteon;
   (b) selecting at least one database comprising empirical data based on recorded observations of at least one parameter in a selected region of the subject bone osteon, wherein the selected region of the subject bone osteon comprises an interface between a lacuna and extracellular matrix (ECM) in the subject bone osteon, and wherein the at least one parameter is collagen bundle orientations;
   (c) using the database with a first computer program to generate a simulated region of the subject bone osteon, the simulated region comprising a perilacunar region of the selected region of the subject bone osteon, wherein the first computer program performs the steps of:
      (1) defining a simulated three-dimensional region corresponding to the simulated perilacunar region of the simulated region of the subject bone osteon;
      (2) creating a finite element mesh defining a finite number of three-dimensional elements filling the simulated three-dimensional region; and
      (3) assigning collagen bundle orientation to each of a plurality of the elements in the finite element mesh using data from the database; and
   (d) using a second computer program to predict a mechanical response of the selected region of the subject bone osteon to an applied force, wherein the second computer program performs the steps of:
      (1) generating a simulated force applied to the simulated three-dimensional region;
      (2) calculating a response to the simulated force for each of the plurality of elements in the finite element mesh using the assigned collagen bundle orientation for each element;
      (3) computing a response of the simulated three-dimensional region to the simulated force using the calculated responses of the plurality of elements in the finite element mesh;
      (4) computing the mechanical response of the simulated region of the subject bone osteon as a function of collagen bundle orientation using the computed response of the simulated three-dimensional region to the simulated force; and
      (5) outputting the computed mechanical response of the selected region of the subject bone osteon to the simulated force.

2. The method of claim 1, wherein the selected region of the subject bone osteon is the interface between osteocyte lacunae and calcified ECM in a secondary osteon.

3. The method of claim 2, wherein the parameter is collagen bundle orientation that is circumambiently perpendicular along the lateral side of the lacunar-ECM interface.

4. The method of claim 1, wherein the parameter is collagen bundle orientation at the perilacunar region that is circumambiently perpendicular to the lacuna.

5. The method of claim 1, wherein the selected region of the subject bone osteon comprises a sharp or round apex of the lacuna.

6. The method of claim 1, wherein the empirical data comprises a stress distribution generated by the collagen bundle orientation.

7. A tangible computer-readable storage medium embodying information indicative of instructions for causing one or more machines to perform operations for predicting a mechanical response of a region of a subject bone osteon to an applied force, comprising:
   (a) a database comprising empirical data corresponding to recorded observations of at least one parameter in a selected region of the subject bone osteon, wherein the selected region of the subject bone osteon comprises an interface between a lacuna and extracellular matrix (ECM), and wherein the at least one parameter is collagen bundle orientations in the selected region of the subject bone osteon; and
   (b) a set of computer readable instructions for use with the database comprising:
      (1) instructions for generating a simulated region of the subject bone osteon wherein the simulated region comprises a perilacunar region of the selected region of the subject bone osteon;
      (2) instructions for defining a simulated three-dimensional region corresponding to the simulated perilacunar region of the simulated region of the subject bone osteon;
      (3) instructions for creating a finite element mesh defining a finite number of three-dimensional elements filling the simulated three-dimensional region;
      (4) instructions for assigning collagen bundle orientation to each of a plurality of the elements in the finite element mesh using data from the database;
      (5) instructions for applying a simulated force to the simulated three-dimensional region;
      (6) instructions for calculating a response to the simulated force for each of the plurality of elements in the finite element mesh using the assigned collagen bundle orientation for each element;
      (7) instructions for computing a response of the simulated three-dimensional region to the simulated force using the calculated responses of the plurality of elements in the finite element mesh;
      (8) instructions for computing the mechanical response of the simulated region of the subject bone osteon as a function of collagen bundle orientation using the computed response of the simulated three-dimensional region to the simulated force; and
      (9) instructions for outputting the computed mechanical response of the selected region of the subject bone osteon to the simulated force.

8. The computer-readable storage medium of claim 7, wherein the selected region of the subject bone osteon is the interface between osteocyte lacunae and calcified ECM in a secondary osteon.

9. The computer-readable storage medium of claim 8, wherein the parameter is collagen bundle orientation that is circumambiently perpendicular along the lateral side of the lacunar-ECM interface.

10. The computer-readable storage medium of claim 7, wherein the parameter is collagen bundle orientation at the perilacunar region that is circumambiently perpendicular to the lacuna.

11. The computer-readable storage medium of claim 7, wherein the selected region of the subject bone osteon comprises a sharp or round apex of the lacuna.

12. The computer-readable storage medium of claim 7, wherein the empirical data comprises a stress distribution generated by the collagen bundle orientation.

* * * * *